(12) United States Patent
Ryan

(10) Patent No.: US 12,151,076 B2
(45) Date of Patent: Nov. 26, 2024

(54) HIGH FLOW, NEEDLELESS CONNECTOR

(71) Applicant: RyMed Technologies, LLC, Austin, TX (US)

(72) Inventor: Dana Wm. Ryan, Mt. Juliet, TN (US)

(73) Assignee: RyMed Technologies, LLC, Austin, TX (US)

( * ) Notice: Subject to any disclaimer, the term of this patent is extended or adjusted under 35 U.S.C. 154(b) by 0 days.

(21) Appl. No.: 18/513,818

(22) Filed: Nov. 20, 2023

(65) Prior Publication Data

US 2024/0082561 A1 Mar. 14, 2024

Related U.S. Application Data

(62) Division of application No. 17/022,231, filed on Sep. 16, 2020, now Pat. No. 11,857,752.

(60) Provisional application No. 62/948,546, filed on Dec. 16, 2019.

(51) Int. Cl.
*A61M 39/14* (2006.01)
*A61M 39/10* (2006.01)
*A61M 39/26* (2006.01)

(52) U.S. Cl.
CPC .......... *A61M 39/146* (2013.01); *A61M 39/26* (2013.01); *A61M 2039/1083* (2013.01); *A61M 2039/1088* (2013.01); *A61M 2039/267* (2013.01)

(58) Field of Classification Search
CPC ............. A61M 39/146; A61M 39/26; A61M 2039/1083; A61M 2039/1088; A61M 2039/267
See application file for complete search history.

(56) References Cited

U.S. PATENT DOCUMENTS

| | | | |
|---|---|---|---|
| 5,782,819 A | 7/1998 | Tanzer et al. |
| 5,788,215 A | 8/1998 | Ryan |
| 5,830,195 A | 11/1998 | Peters et al. |
| 5,833,213 A | 11/1998 | Ryan |
| 5,954,313 A | 9/1999 | Ryan |
| 6,113,068 A | 9/2000 | Ryan |
| 6,299,131 B1 | 10/2001 | Ryan |
| 6,994,315 B2 | 2/2006 | Ryan et al. |
| 7,530,546 B2 | 5/2009 | Ryan et al. |
| 7,600,530 B2 | 10/2009 | Truitt et al. |
| 7,771,383 B2 | 8/2010 | Truitt et al. |
| 8,096,525 B2 | 1/2012 | Ryan |
| 8,298,196 B1 | 10/2012 | Mansour |

(Continued)

FOREIGN PATENT DOCUMENTS

| | | |
|---|---|---|
| JP | 2013510690 A | 3/2013 |
| WO | 2012103518 A2 | 8/2012 |

OTHER PUBLICATIONS

International Search Report and Written Opinion for corresponding PCT/US2020/062192, dated May 12, 2021, 17 pages (not prior art).

*Primary Examiner* — Theodore J Stigell
(74) *Attorney, Agent, or Firm* — Lucian Wayne Beavers; Patterson Intellectual Property Law, PC

(57) ABSTRACT

An intermittent, injection port assembly includes a flexible valve member of the type which is laterally deflected when moved from a closed position to an open position. A high flow non-tortuous flow passage is provided through the injection port assembly by a plurality of lateral passages bypassing a base which supports the flexible valve member.

10 Claims, 20 Drawing Sheets

(56) References Cited

U.S. PATENT DOCUMENTS

| | | |
|---|---|---|
| 8,715,222 B2 | 5/2014 | Truitt et al. |
| 8,840,577 B1 | 9/2014 | Zollinger et al. |
| 8,951,233 B2 | 2/2015 | Mansour |
| 9,278,206 B2* | 3/2016 | Fangrow ................. A61M 39/10 |
| 9,375,561 B2 | 6/2016 | Mansour et al. |
| 9,782,576 B2 | 10/2017 | Truitt et al. |
| 9,925,365 B1 | 3/2018 | Ryan et al. |
| 10,010,711 B2 | 7/2018 | Mansour |
| 10,105,529 B2 | 10/2018 | Ryan |
| 10,220,419 B2 | 3/2019 | Ryan et al. |
| 10,238,858 B2 | 3/2019 | Ueda et al. |
| 10,258,786 B2 | 4/2019 | Truitt et al. |
| 10,357,645 B2 | 7/2019 | Ryan et al. |
| 10,449,575 B2 | 10/2019 | Ryan et al. |
| 2009/0299300 A1 | 12/2009 | Truitt et al. |
| 2011/0282302 A1* | 11/2011 | Lopez ................... A61M 39/26 |
| | | 604/246 |
| 2011/0319859 A1* | 12/2011 | Zeytoonian ......... A61M 39/045 |
| | | 604/246 |
| 2012/0310179 A1 | 12/2012 | Truitt et al. |
| 2012/0316514 A1 | 12/2012 | Mansour |
| 2014/0276459 A1* | 9/2014 | Yeh ....................... A61M 39/26 |
| | | 604/256 |
| 2014/0276460 A1* | 9/2014 | Zollinger .............. A61M 39/22 |
| | | 604/256 |
| 2017/0281824 A1 | 10/2017 | Ryan et al. |
| 2018/0289943 A1 | 10/2018 | Ryan |
| 2018/0369563 A1 | 12/2018 | Ryan et al. |
| 2019/0134303 A1 | 5/2019 | Ryan et al. |
| 2019/0329020 A1 | 10/2019 | Ryan et al. |

* cited by examiner

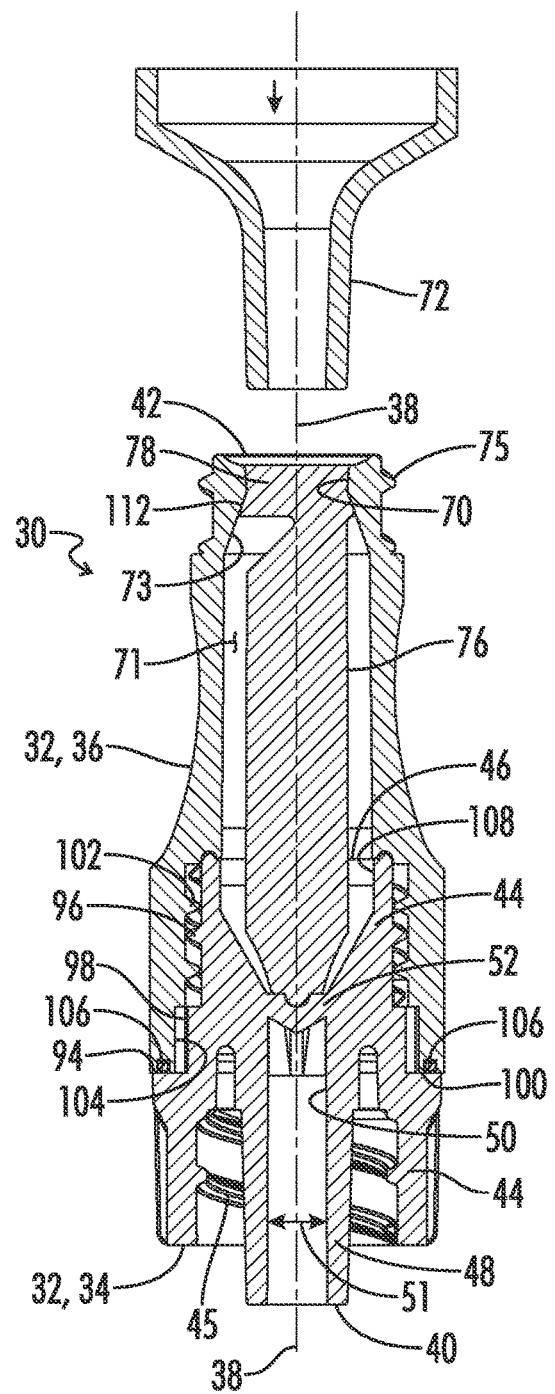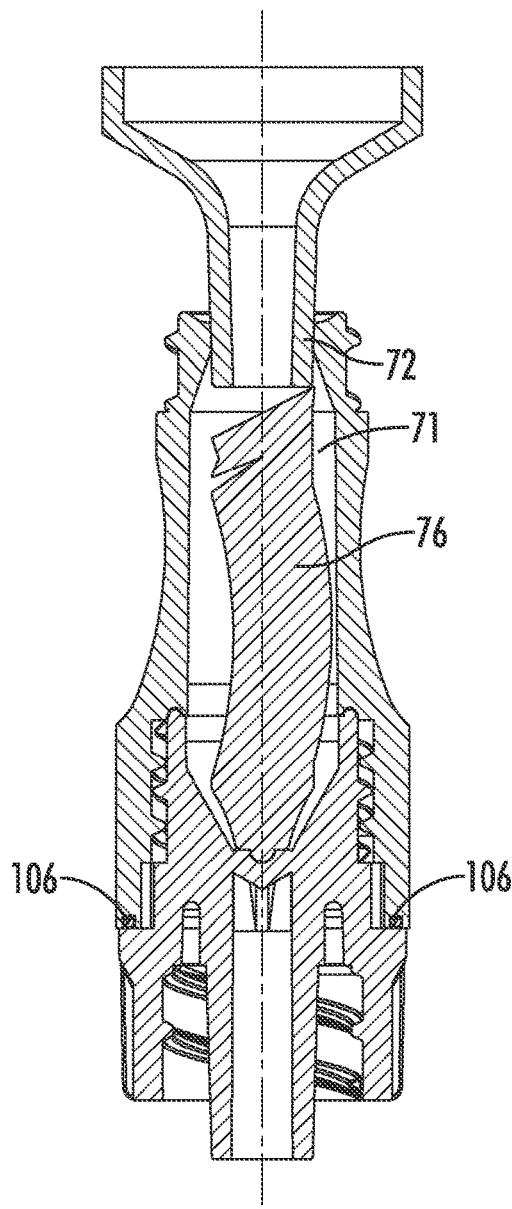
FIG. 1
FIG. 2

HIGH FLOW, NEEDLELESS CONNECTOR

CROSS-REFERENCE TO RELATED APPLICATIONS

This application is a divisional of U.S. patent application Ser. No. 17/022,231 filed Sep. 16, 2020, which claims priority of provisional application Ser. No. 62/948,546 filed Dec. 16, 2019, entitled HIGH FLOW, NEEDLELESS CONNECTOR, the details of which are incorporated herein by reference.

BACKGROUND OF THE INVENTION

1. Field of the Invention

The present application relates to needleless connectors, also referred to as intermittent injection port assemblies, used to provide safe connections for infusion of IV fluids, antibiotics, lipids, blood, blood components or drug products and/or blood aspiration in intravenous and blood administration therapies.

2. Description of the Prior Art

One type of needleless connector that is known in the art uses an internal valve member having a hollow cannula which pierces a slit in a flexible valve member as the flexible valve member is axially compressed. One example of connectors of this type is seen in Ryan U.S. Pat. No. 9,925,365.

A second type of known needleless connector uses a flexible valve member that is laterally displaced when it is moved to an open position. One example of connectors of this type is seen in We Schmidt U.S. Pat. No. 5,782,816.

There is a continuing need in needleless connectors of both of these types for improvements that allow for improved performance, and for less expensive methods of construction.

SUMMARY OF THE INVENTION

In one embodiment an injection port assembly includes a body including a first mating structure and a second mating structure configured to be coupled to the first mating structure. The body has a central body axis extending from a distal body end defined on the first mating structure to a proximal body end defined on the second mating structure. The first mating structure includes an annular wall defining an open proximal end of the first mating structure facing toward the proximal body end. A male luer connection includes an axial passage extending from a distal end of the male luer connection toward the proximal body end. A base is centered on the body axis and at least partially blocks the axial passage. A plurality of circumferentially spaced ribs extend from the annular wall to the base and define a plurality of transverse passages between the circumferentially spaced ribs. The transverse passages communicate with the axial passage of the male luer connection. The second mating structure includes a female luer connection configured to receive a male luer fitting, such as a syringe or IV line. The second mating structure has an interior communicating the female luer connection with the open proximal end of the first mating structure. A flexible valve member is mounted on the base of the first mating structure and has a proximal valve end portion configured to be sealingly received in the female luer connection of the second mating structure when the flexible valve member is in a closed position. The flexible valve member is configured to be displaced relative to the central body axis upon entry of the male luer fitting into the female luer connection to thereby place the male luer fitting in communication with the interior of the second mating structure.

In another embodiment the injection port assembly includes a body including a first mating structure and a second mating structure configured to be coupled to the first mating structure. The body has a central body axis extending from a distal body end defined on the first mating structure to a proximal body end defined on the second mating structure. The first mating structure may include an outer wall defining an open proximal end of the first mating structure facing toward the proximal body end. An inner cylindrical surface may extend distally from the open proximal end of the first mating structure. The inner cylindrical surface may have a first inner diameter. A male luer connection may be connected to the outer wall and extend distally to a free end. The male luer connection may include an axial passage, the axial passage having a second inner diameter smaller than the first inner diameter. A base may span the body axis and be supported from the outer wall. The base may be located axially between the open proximal end of the first mating structure and the axial passage of the male luer connection. A plurality of transverse passages partially frusto-conical in shape tapering from the first inner diameter of the inner cylindrical surface to the second inner diameter of the axial passage of the male luer connection may bypass the base and communicate the inner cylindrical surface with the axial passage of the male luer connection. The second mating structure may include a female luer connection configured to receive a male luer fitting. The second mating structure may have an interior communicating the female luer connection with the open proximal end of the first mating structure. A flexible valve member may have a proximal end portion configured to be sealingly received in the female luer connection of the said second mating structure when the flexible valve member is in a closed position. The flexible valve member may be configured to be laterally displaced relative to the central body axis upon entry of the male luer fitting into the female luer connection to thereby place the male luer fitting in communication with the interior of the second mating structure.

In any of the above embodiments the first mating structure may include a centering recess defined in the base and facing the proximal body end. The flexible valve member may include a distal end having a central protrusion received in the centering recess.

In any of the above embodiments each rib may include a proximal end face sloping distally from a radially outer end of the rib to a radially inner end of the rib attached to the base, so that the proximal end faces of the ribs define a tapered guide for guiding a distal end of the flexible valve member into engagement with the base.

In any of the above embodiments the axial passage of the male luer connection may have an inside diameter, and the base may have an outside diameter substantially equal to the inside diameter of the axial passage of the male luer connection.

In any of the above embodiments the second mating structure may include an annular radially inner distally facing step. The open proximal end of the first mating structure may about the distally facing step of the second mating structure when the first and second mating structures are coupled together. One of the distally facing step of the second mating structure and the open proximal end of the first mating structure may include an annular groove, and the other of the distally facing step of the second mating structure and the open proximal end of the first mating structure may include an annular ridge received in the annular groove to provide a seal between the first and second mating structures.

In any of the above embodiments an O-ring seal may be provided between the first and second mating structures for additional sealing functionality.

In any of the above embodiments the first mating structure may include an inner cylindrical surface extending distally from the open proximal end of the first mating structure, the inner cylindrical surface having a first diameter. The axial passage of the male Luer connection may have a second inner diameter smaller than the first inner diameter. The transverse passages may be partially frusto-conical in shape tapering from the first inner diameter to the second inner diameter.

In any of the above embodiments the base may have a base outside diameter substantially equal to the second inside diameter.

In any of the above embodiments the first and second mating structures may be first and second integrally molded plastic parts, respectively.

In any of the above embodiments a threaded connection may be provided between the first and second mating structures, and a ratchet lock may be provided to prevent unthreading of the threaded connection after the first and second mating structures are coupled together by the threaded connection.

In another embodiment an injection port assembly includes a body including a first mating structure and a second mating structure configured to be coupled to the first mating structure. The body may have a central body axis extending from a distal body end defined on the first mating structure to a proximal body end defined on the second mating structure. The first mating structure may include a first mating structure proximal end, a radially outer proximally facing step, an external thread located between the first mating structure proximal end and the radially outer proximally facing step, and a first annular ratchet portion. The second mating structure may include an annular radially inner distally facing step, a second mating structure distal end, an internal thread located between the second mating structure distal end and the radially inner distally facing step, and a second annular ratchet portion. The first and second mating structures may be configured to be coupled together by engagement of the internal thread with the external thread such that the first and second annular ratchet portions prevent disengagement of the internal thread from the external thread after the first and second mating structures are coupled together.

The first mating structure proximal end may abut the annular radially inner distally facing step of the second mating structure when the first and second mating structures are coupled together. One of the annular radially inner distally facing step of the second mating structure and the first mating structure proximal end may include an annular groove, and the other may include an annular ridge received in the annular groove to provide a seal between the first and second mating structures.

In another embodiment an injection port assembly includes a body including a first mating structure and a second mating structure configured to be coupled to the first mating structure. The body has a central body axis extending from a distal body end defined on the first mating structure to a proximal body end defined on the second mating structure. The first mating structure includes an annular wall defining an open proximal end of the first mating structure facing toward the proximal body end. A male luer connection includes an axial passage extending from a distal end of the male luer connection toward the proximal body end. An internal passage communicates the open proximal end of the first mating structure with the axial passage of the male luer connection. The second mating structure includes a female luer connection configured to receive a male luer fitting, such as a syringe or IV line. The second mating structure has an interior communicating the female luer connection with the open proximal end of the first mating structure. A flexible valve member is mounted on the first mating structure and has a proximal valve end portion configured to be sealingly received in the female luer connection of the second mating structure when the flexible valve member is in a closed position. The flexible valve member includes an axially extending main body portion, a tapered distal end portion extending distally from the main body portion, and a tapered proximal portion extending proximally from the main body portion to the proximal valve end portion. The tapered distal end portion engages the first mating structure. The tapered proximal portion is axially longer than the tapered distal end portion. The flexible valve member further includes a plurality of stabilizing fins extending laterally outward from the main body portion toward the interior wall of the second mating structure. The tapered proximal portion is configured to buckle asymmetrically relative to the central body axis upon entry of the male luer fitting into the female luer connection to thereby place the male luer fitting in communication with the interior of the second mating structure.

The main body portion of the flexible valve member may be cylindrical in shape having a main body portion diameter.

The main body portion may have a main body portion length at least one-half an axial length of the flexible valve member.

The tapered proximal portion may taper from the main body portion diameter to a minimum outside diameter less than 60% of the main body portion diameter.

The tapered proximal portion may have an axial length greater than the main body portion diameter.

The tapered proximal portion may have an axial length greater than 125% of the main body portion diameter.

In another embodiment an injection port assembly includes a body including a first mating structure and a second mating structure configured to be coupled to the first mating structure. The body has a central body axis extending from a distal body end defined on the first mating structure to a proximal body end defined on the second mating structure. The first mating structure includes an annular wall defining an open proximal end of the first mating structure facing toward the proximal body end. A male luer connection includes an axial passage extending from a distal end of the male luer connection toward the proximal body end. An internal passage communicates the open proximal end of the first mating structure with the axial passage of the male luer connection. The first mating structure may include a radially outer proximally facing step, and a cylindrical outer wall surface located between the proximal end of the first mating structure and the radially outer proximally facing step. The second mating structure includes a female luer connection configured to receive a male luer fitting, such as a syringe or IV line. The second mating structure has an interior communicating the female luer connection with the open proximal end of the first mating structure. A flexible valve member is mounted on the first mating structure and has a proximal valve end portion configured to be sealingly received in the female luer connection of the second mating structure when the flexible valve member is in a closed position. The second mating structure may include an annular radially inner distally facing step defined in the interior wall. A cylindrical inner surface may be located on the second mating structure between a second mating structure distal end and the radially inner distally facing step. The cylindrical outer wall surface of the first mating structure may be closely received in and sonically welded to the cylindrical inner surface of the second mating structure.

The first mating structure may further include a proximally facing radially outward extending step located distally of the open proximal end of the first mating structure. The second mating structure distal end may engage and be sonically welded to the proximally facing radially outward extending step of the first mating structure.

The proximally facing radially outward extending step of the first mating structure further may include a proximally facing annular groove configured to receive weld slag generated during the sonic welding of the second mating structure distal end to the proximally facing radially outward extending step of the first mating structure.

Numerous objects, features and advantages of the embodiments set forth herein will be readily apparent to those skilled in the art upon reading of the following disclosure when taken in conjunction with the accompanying drawings.

BRIEF DESCRIPTION OF THE DRAWINGS

FIG. 1 is a cross-section elevation view of the injection port assembly with the flexible valve member in a closed position. A male luer syringe tip is shown above the injection port assembly prior to engaging the flexible valve member.

FIG. 2 is a cross-section elevation view of the injection port assembly of FIG. 1 showing the male luer syringe tip engaging the flexible valve member so that the flexible valve member is moved to an open position.

FIG. 3 is taken along line 3-3 of FIG. 9.

FIG. 4 is taken along line 4-4 of FIG. 5.

FIG. 11 is taken along line 11-11 of FIG. 12.

FIG. 15 is taken along line 15-15 of FIG. 16.

FIG. 27 is taken along line 27-27 of FIG. 26.

FIG. 29 is taken along line 29-29 of FIG. 28.

DETAILED DESCRIPTION

Embodiment of FIGS. 1-23

Figure 3:
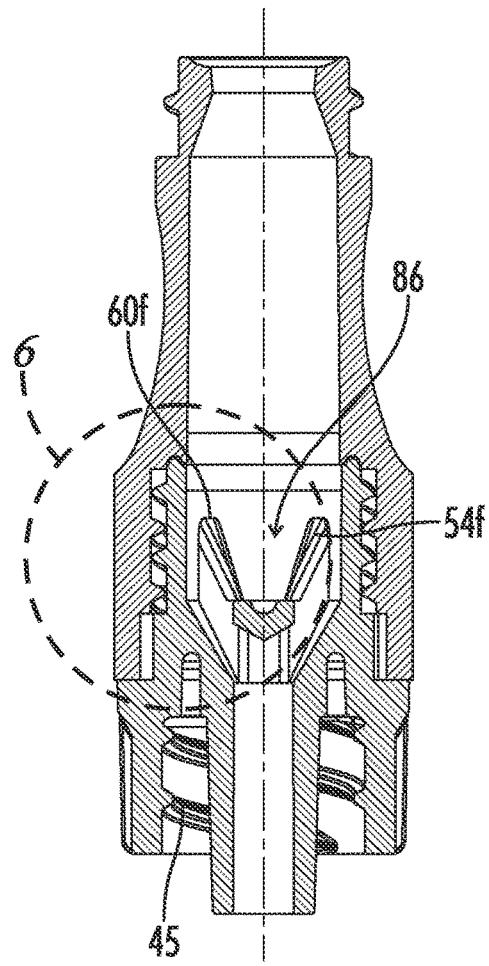
FIG. 3 is a cross-section elevation view of the first and second mating structures of the body of the injection port assembly, shown in an assembled position. The flexible valve member has been removed for clarity.

Referring now to the drawings and particularly to FIG. 1 an injection port assembly is shown and generally designated by the number 30. The injection port assembly 30 may also be referred to as an intermittent needleless connector 30. The injection port assembly 30 includes a body 32 including a first mating structure 34 and the second mating structure 36 configured to be coupled to the first mating structure 34. Each of the first and second mating structures 34 and 36 may be a separate integrally molded plastic part.

The body 32 has a central body axis 38 extending from a distal body end 40 defined on the first mating structure 34 to a proximal body end 42 defined on the second mating structure 36.

The first mating structure 34 includes an annular wall 44 defining an open proximal end 46 of the first mating structure 34 facing toward the proximal body end 42. A male luer connection 48 includes an axial passage 50 extending from a distal end 40 of the male Luer connection which is coincident with the distal end 40 of the body 30. The open proximal end 46 may also be referred to as a first mating structure proximal end 46. Annular wall 44 may also be referred to as an outer wall 44 and extends distally past a base 52 and includes an internal thread 45 concentric with the male luer connection 48.

Figure 7:
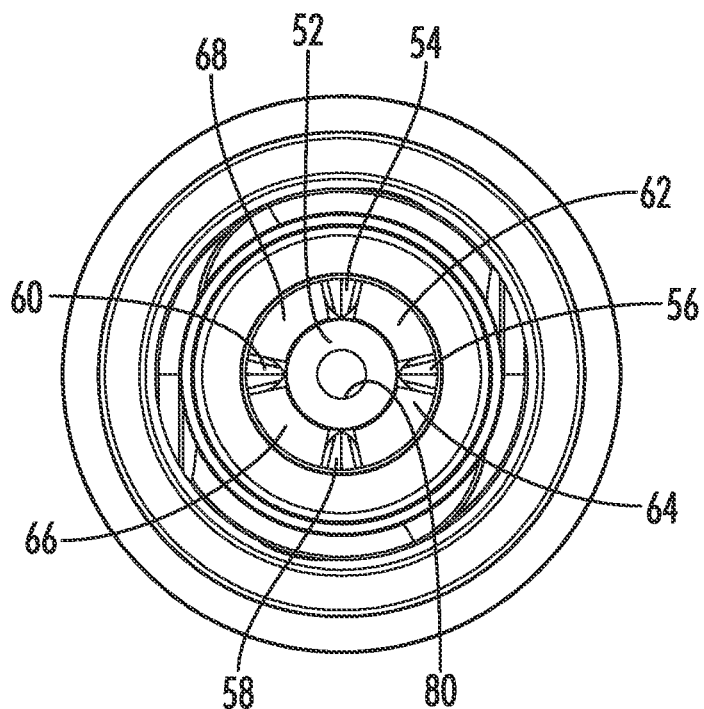
FIG. 7 is a top end view of the body of FIG. 5.

The base 52 is centered on the body axis 38 and at least partially blocks the axial passage 50. As best seen in FIG. 7 a plurality of circumferentially spaced ribs 54, 56, 58 and 60 extend from the annular wall 44 to the base 52 and define a plurality of transverse passages 62, 64, 66 and 68 between the circumferentially spaced ribs. The transverse passages are communicated with the axial passage 50 of the male luer connection 48. The transverse passages may also be described as bypassing the base 52 to communicate an inner cylindrical surface 108 of the first mating structure 34 with the axial passage 50 of the male luer connection 48. The base 52 may also be described as spanning the body axis 38 and being supported from the outer wall 44. The base 52 may also be described as being located axially between the open proximal end 46 of the first mating structure 34 and the axial passage 50 of the male luer connection 48.

The axial passage 50 has an inside diameter 51. The base 52 has a base outside diameter 53 substantially equal to the inside diameter 51 of the axial passage 50 of the male luer connection 48.

The use of the multiple transverse passages 62, 64, 66 and 68 provides a combined flow path from the open proximal end 46 to the axial passage 51 that is relatively unrestricted. The passages 62, 64, 66 and 68 have a combined cross-sectional flow area at least as great as, and preferably greater than, the cross-sectional area of the axial passage 51. Also the passages 62, 64, 66 and 68 are preferably sloped in a range of from 40 to 60 degrees relative to the longitudinal axis 38. In this manner the flow path through the passages 62, 64, 66 and 68 does not restrict the flow of fluids through the injection port assembly 30, thus providing what may be referred to as a high fluid flow injection port assembly. The flow path is non-tortuous and the passages 62, 64, 66 and 68 are free of dead ends or spaces that are difficult to flush of blood and other fluids.

The second mating structure 36 includes a female luer connection 70 configured to receive a male luer fitting 72 (see FIGS. 1 and 2). The second mating structure 36 has an interior 71 communicating the female luer connection 70 with the open proximal end 46 of the first mating structure 34. The upper end of the second mating structure 36 carries an external thread 75 that can be engaged with a luer-lock connector (not shown).

A flexible valve member 76 is mounted on the base 52 of the first mating structure 34 and has a proximal valve end portion 78 configured to be sealingly received in the female luer connection 70 of the second mating structure 36 when the flexible valve member 76 is in a closed position as seen in FIG. 1. The flexible valve member 76 is configured to be displaced relative to the central body axis 38 upon entry of the male luer fitting 72 into the female luer connection 70 to thereby place the male luer fitting 72 in communication with the interior 71 of the second mating structure 36.

The first mating structure 34 includes a centering recess 80 defined in the base 52 and facing the proximal body end 42. The flexible valve member 76 includes a distal end 82 having a central protrusion 84 received in the centering recess 80.

Figure 4:
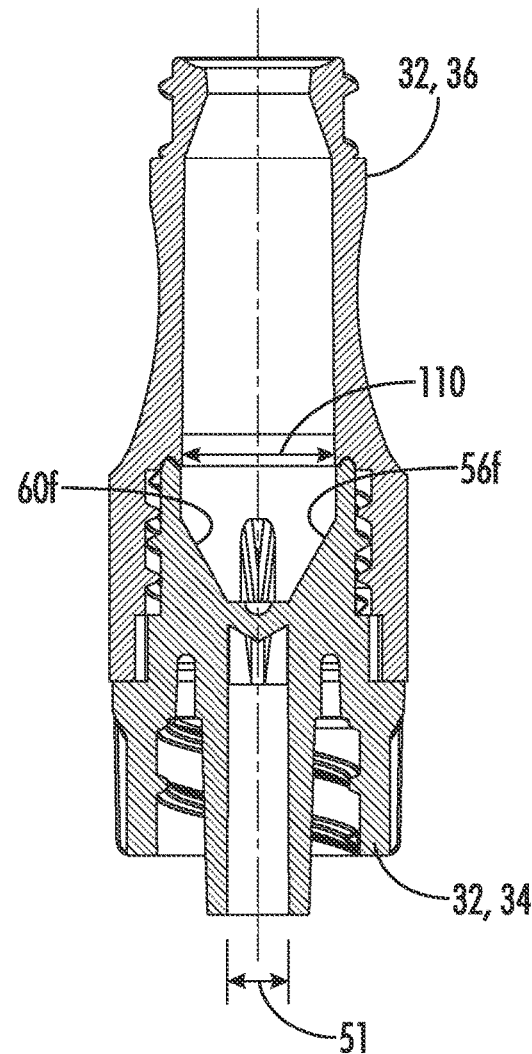
FIG. 4 is a cross-section elevation view like FIG. 3 but rotated 90 degrees about the axis of the body.
Figure 5:
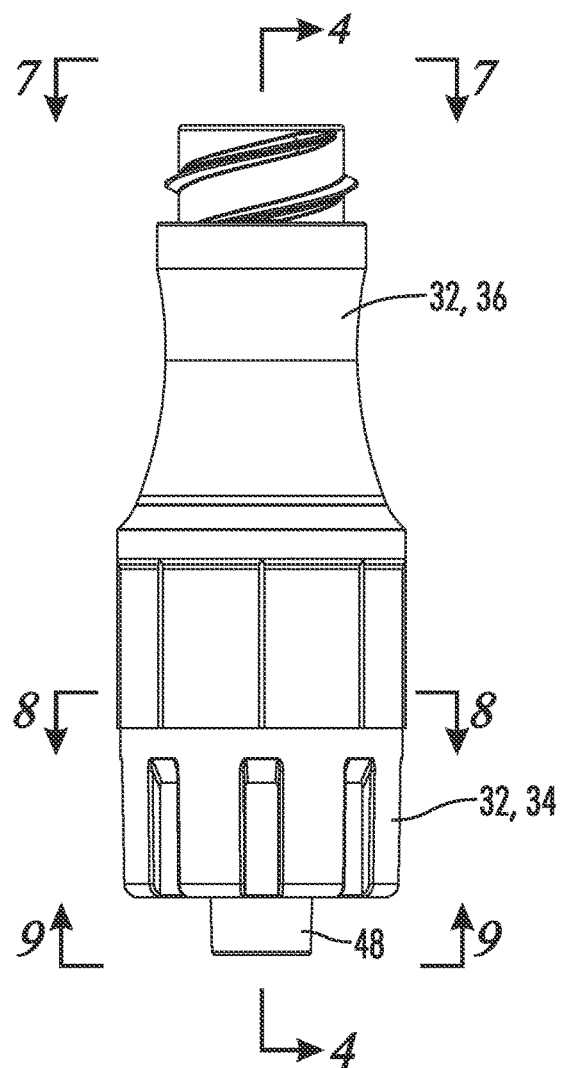
FIG. 5 is an elevation view of the injection port assembly of FIGS. 1-4.

As is best seen in FIGS. 3 and 4 each of the ribs 54, 56, 58 and 60 has a proximal end face such as 54f, 56f, 60f sloping distally from a radially outer end of the rib to a radially inner end of the rib attached to the base 52, so that the proximal end faces of the ribs define a tapered guide 86 for guiding the distal end 82 of the flexible valve member 76 into engagement with the base 52.

The second mating structure 36 includes an annular radially inner distally facing step 88. The open proximal end 46 of the first mating structure 34 abuts the distally facing step 88 of the second mating structure 36 when the first and second mating structures 34 and 36 are coupled together as shown for example in FIGS. 1 and 2. One of the distally facing step 88 of the second mating structure 36 and the open proximal end 46 of the first mating structure 34 includes a groove 90, and the other of the distally facing step 88 of the second mating structure 36 and the open proximal end 46 of the first mating structure 34 includes an annular ridge 92 received in the annular groove 90 to provide a seal between the first and second mating structures 34 and 36.

The ridge 92 may be sized slightly larger than the groove 90, and the second mating structure 36 may have sufficient flexibility about the groove 90 so that a somewhat resilient mating occurs between the ridge 92 and groove 90.

The first mating structure 34 may also include a radially outer proximally facing step 94. An external thread 96 may be located between the first mating structure proximal end 46 and the radially outer proximally facing step 94. A first annular ratchet portion 98 may be located between the external thread 96 and the radially outer proximally facing step 94.

The second mating structure 36 includes the previously mentioned distally facing step 88 and a second mating structure distal end 100. An internal thread 102 may be located between the second mating structure distal end 100 and the radially inner distally facing step 88. A second ratchet portion 104 may be located between the internal thread 102 and the second mating structure distal end 100.

Figure 8:
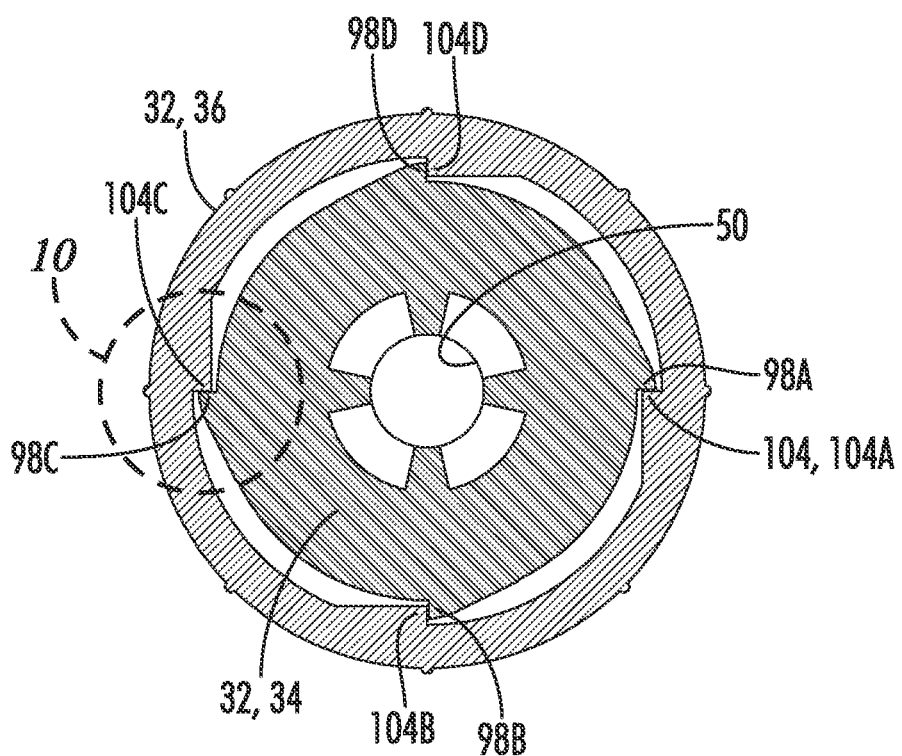
FIG. 8 is a cross-section view taken along line 8-8 of FIG. 5.
Figure 9:
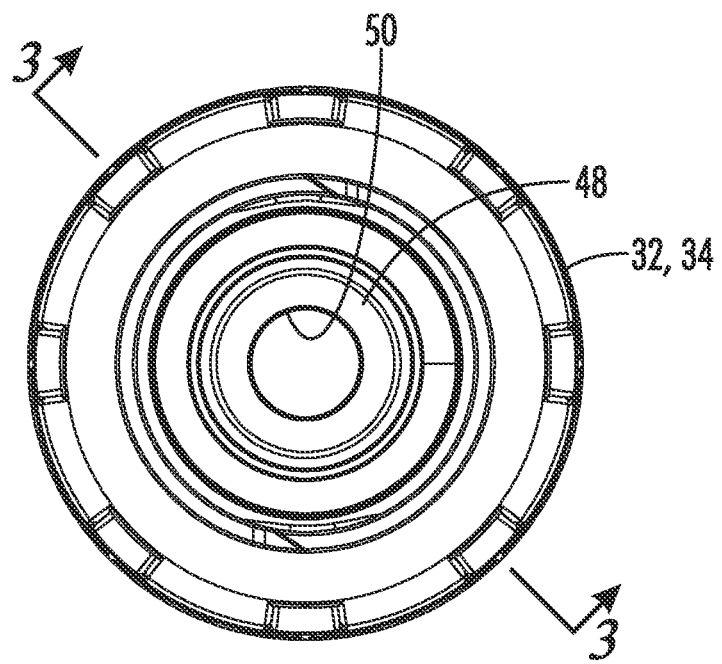
FIG. 9 is a bottom end view of the body of FIG. 5.
Figure 10:
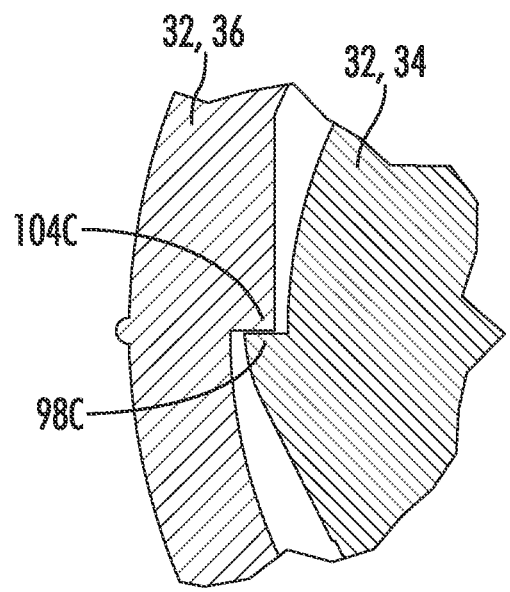
FIG. 10 is an enlarged view of the structure circled in FIG. 8.
Figure 11:
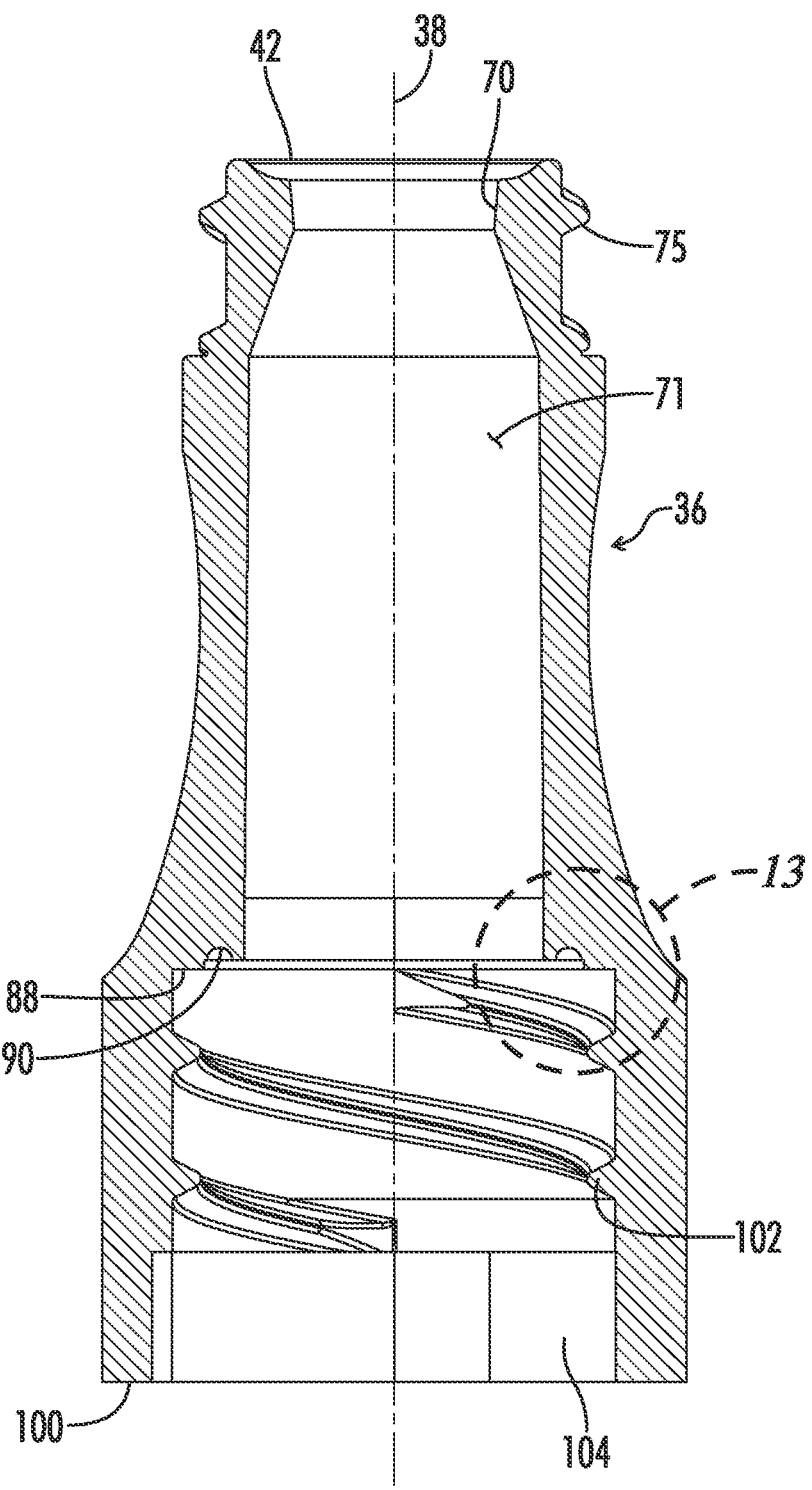
FIG. 11 is a cross-section elevation view of the second mating structure or upper body part of the body of FIG. 3.
Figure 12:
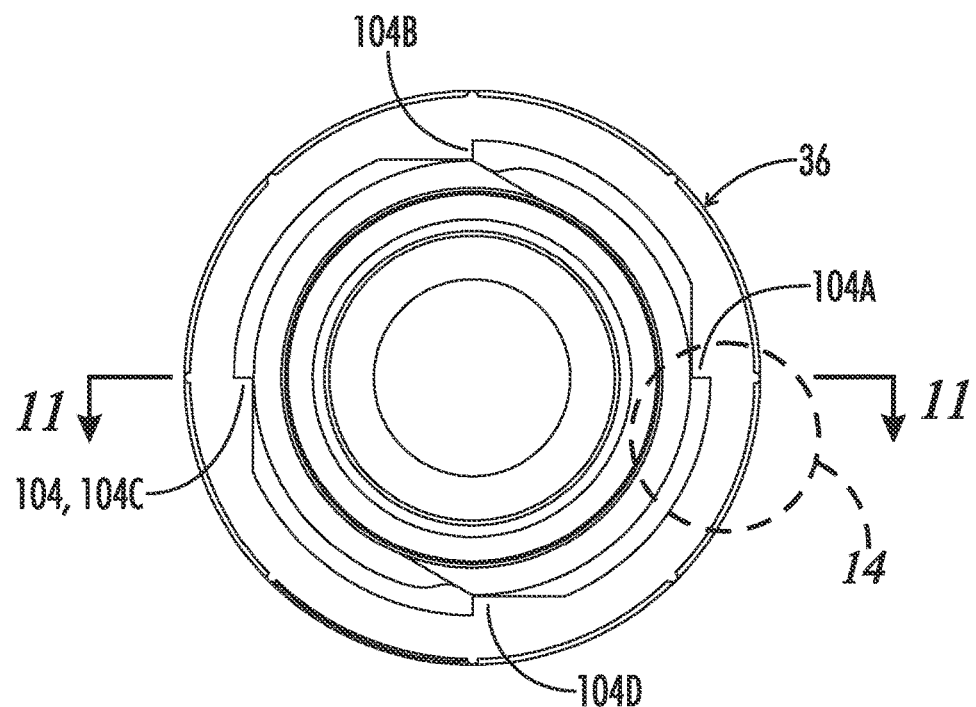
FIG. 12 is a bottom view of the second mating structure of FIG. 11.
Figure 13:
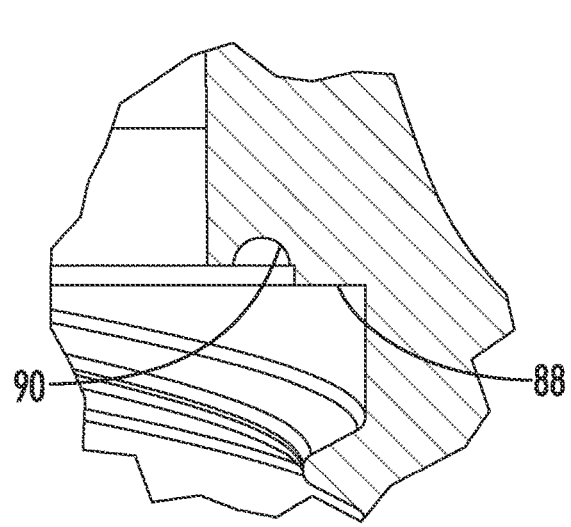
FIG. 13 is an enlarged view of the structure circled in FIG. 11.
Figure 14:
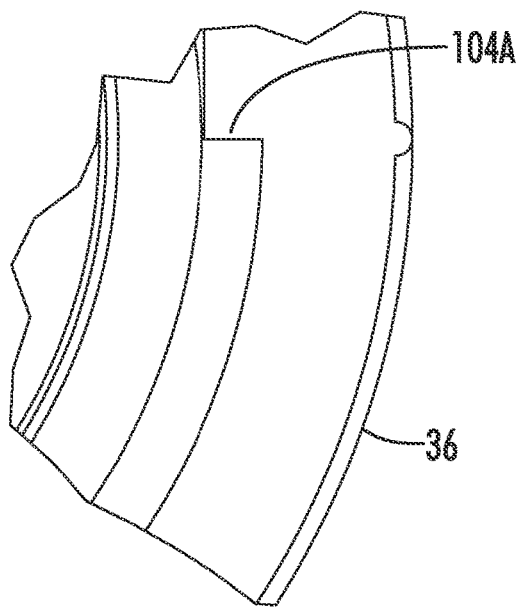
FIG. 14 is an enlarged view of the structure circled in FIG. 12.
Figure 15:
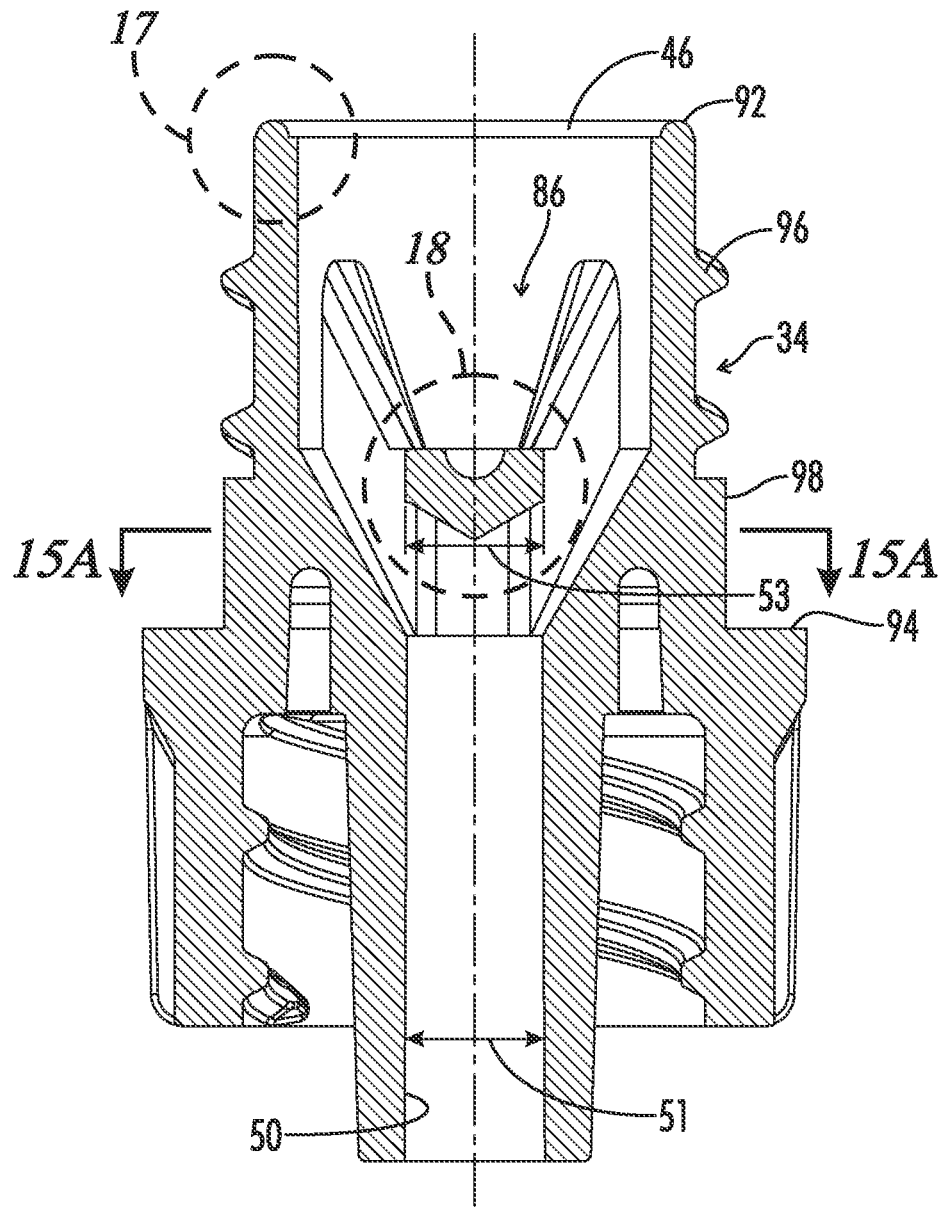
FIG. 15 is a cross-section elevation view of the first mating structure or lower body part of the body of FIG. 3.
Figure 15A:
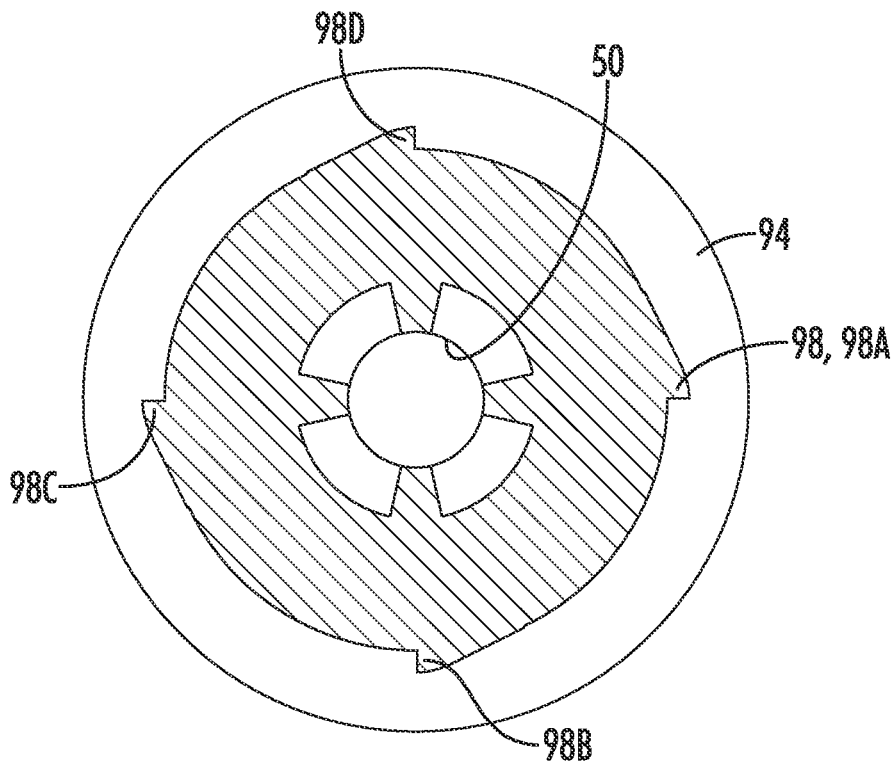
FIG. 15A is a cross-section view taken along line 15A-15A of FIG. 15 showing details of the ratchet.
Figure 16:
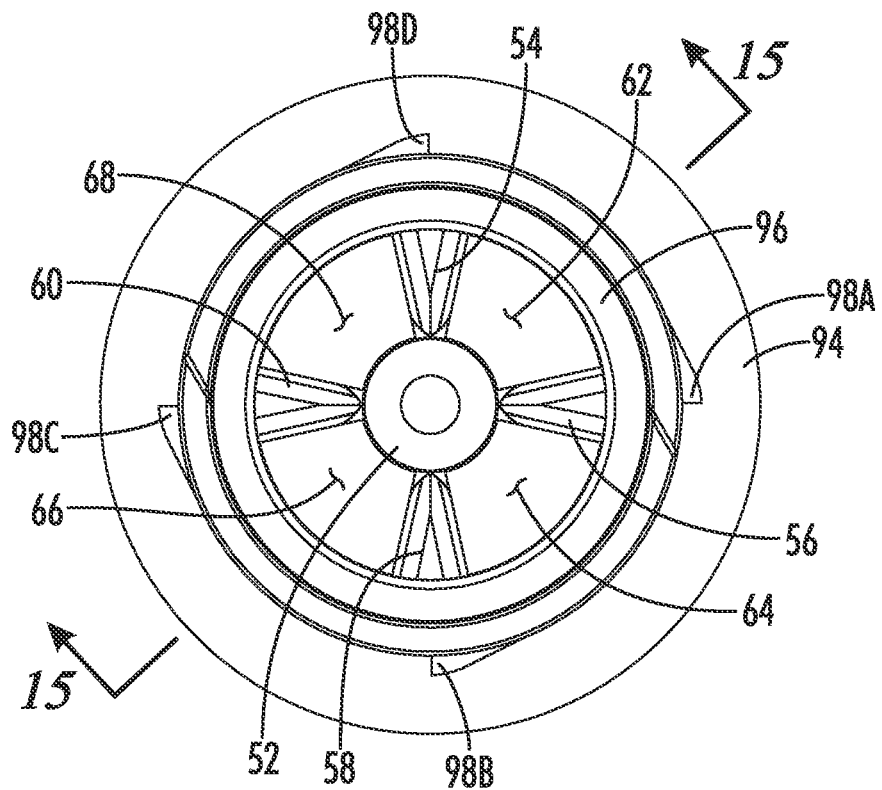
FIG. 16 is a top view of the first mating structure of FIG. 15.
Figure 17:
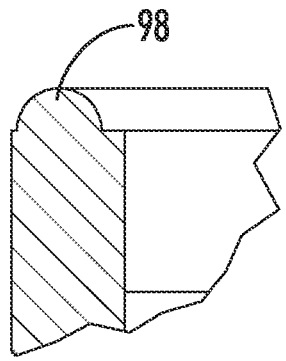
FIG. 17 is an enlarged view of the structure circled in FIG. 15 and identified as 17.
Figure 18:
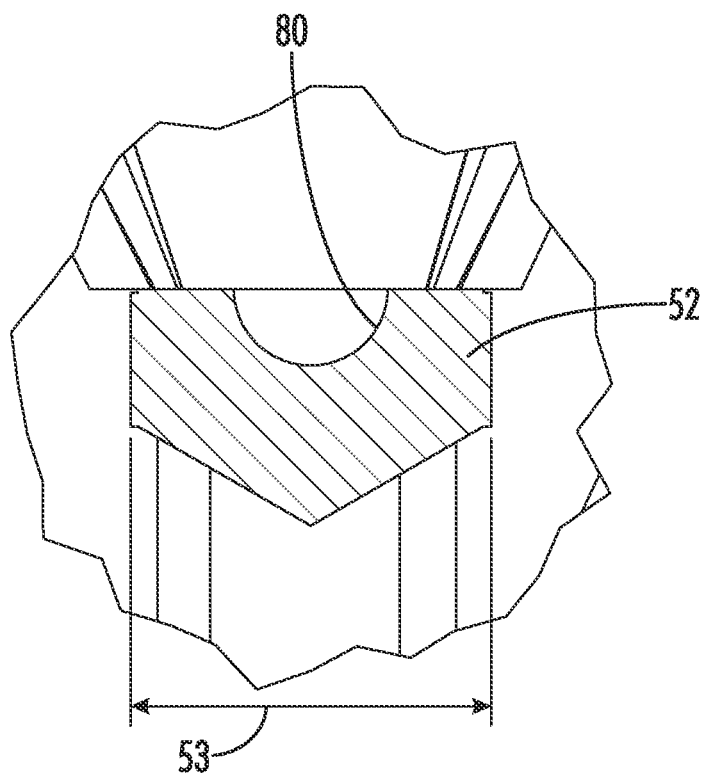
FIG. 18 is an enlarged view of the structure circled in FIG. 15 and identified as 18.
Figure 19:
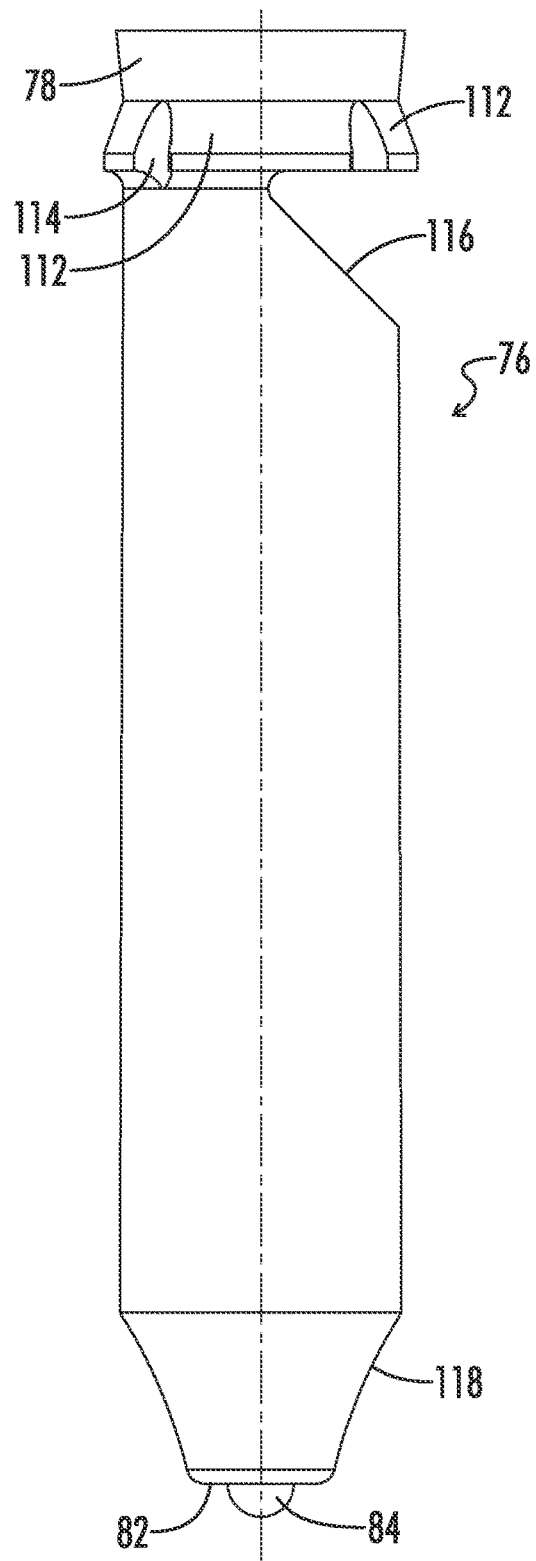
FIG. 19 is an elevation view of the flexible valve member of the injection port assembly of FIG. 1.
Figure 20:
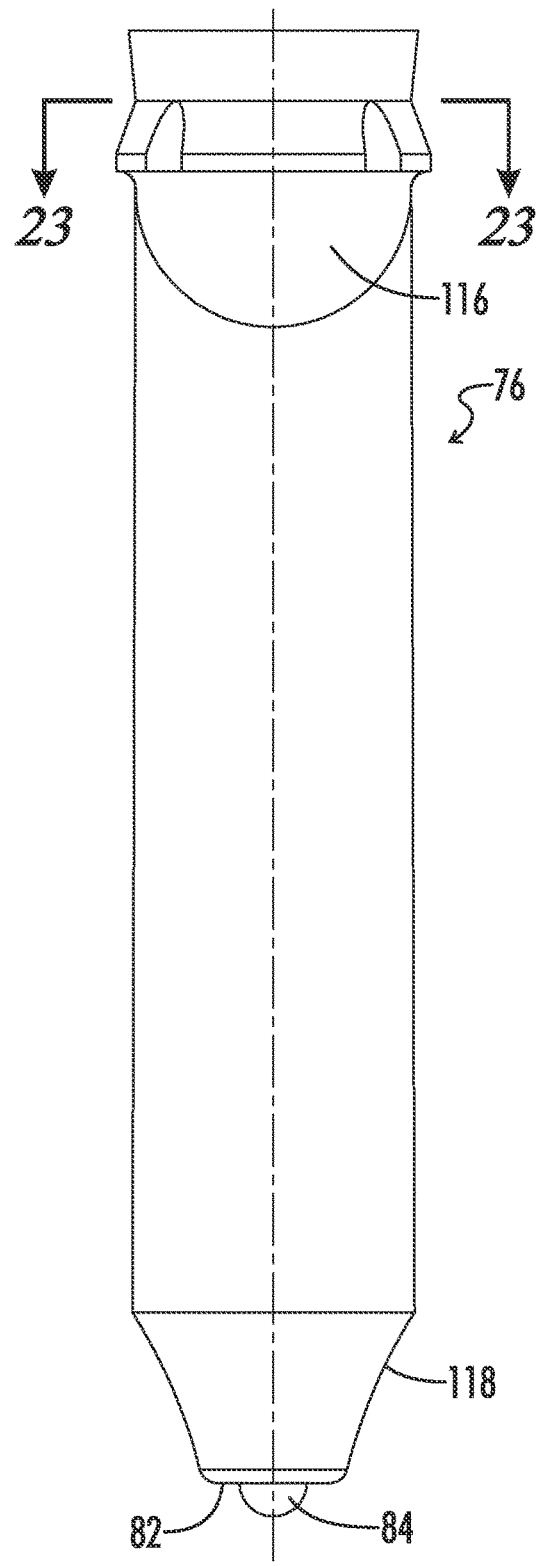
FIG. 20 is another elevation view of the flexible valve member of FIG. 19, rotated 90 degrees about its axis.
Figure 21:
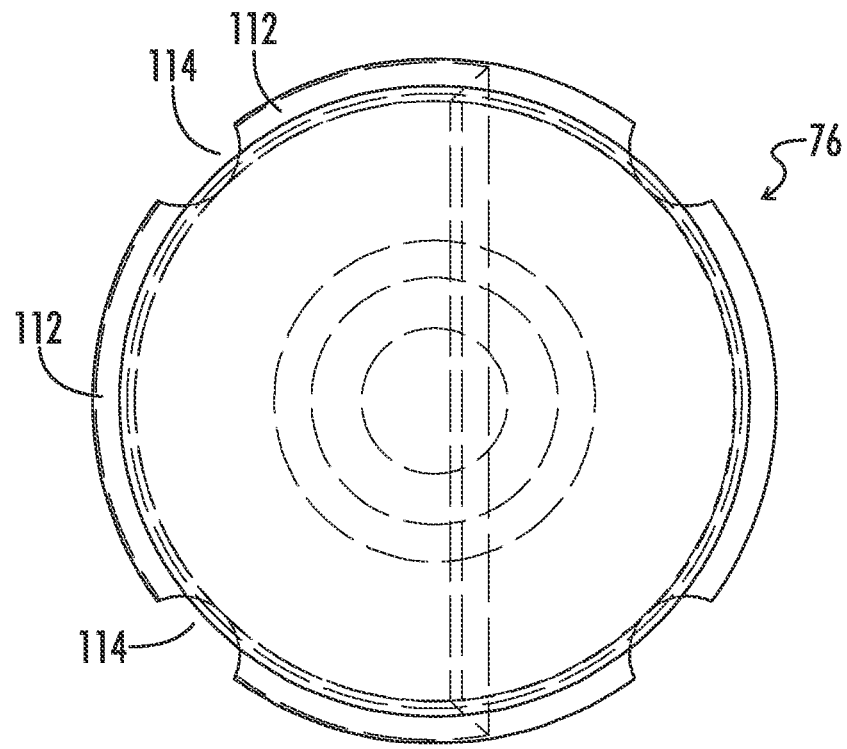
FIG. 21 is a top end view of the flexible valve member of FIG. 19.
Figure 22:
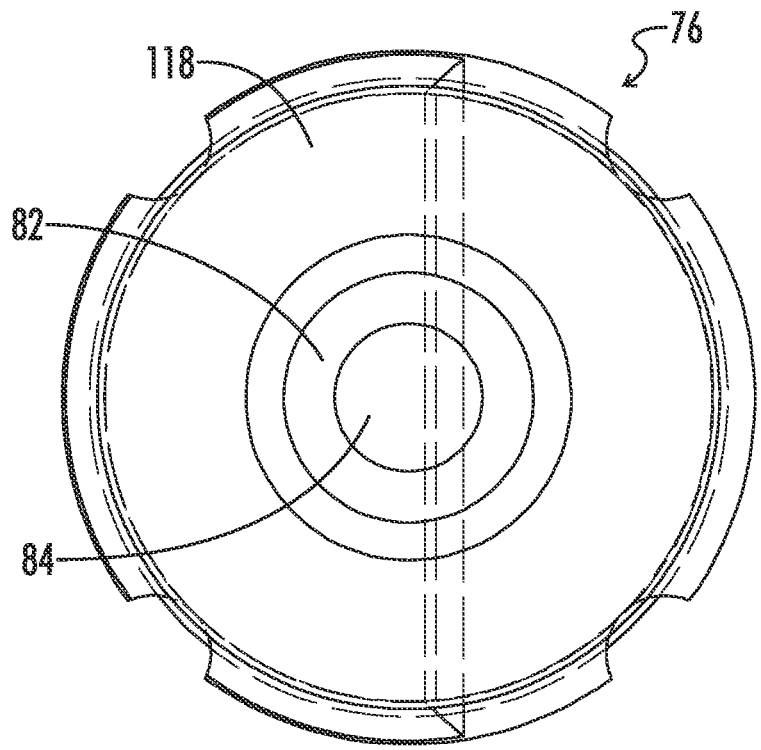
FIG. 22 is a bottom end view of the flexible valve member of FIG. 19.

As best seen in FIG. 15A, the first annular ratchet portion may include four external ratchet teeth 98A, 98B, 98C and 98D. And as best seen in FIG. 8, the second annular ratchet portion 104 may include four internal ratchet teeth 104A, 104B, 104C and 104D.

The first and second mating structures 34 and 36 may be coupled together by engagement of the internal thread 102 with the external thread 96, such that the first and second annular ratchet portions 98 and 104 prevent disengagement of the internal thread 102 from the external thread 96 after the first and second mating structures 34 and 36 are coupled together. The threads 96 and 102 provide a threaded connection between the first and second mating structures 34 and 36. The first and second ratchet portions 98 and 104 provide a ratchet lock configured to prevent unthreading of the threaded connection after the first and second mating structures 34 and 36 are coupled together by the threaded connection.

The threaded connection 96, 102 may provide a seal to prevent passage of any fluid that may pass the seal between groove 90 and ridge 92. Additionally, and optionally, an O-ring seal 106 may be provided between the proximally facing step 94 and the distal end 100. Such an O-ring seal 106 is schematically illustrated in FIG. 2.

Figure 6:
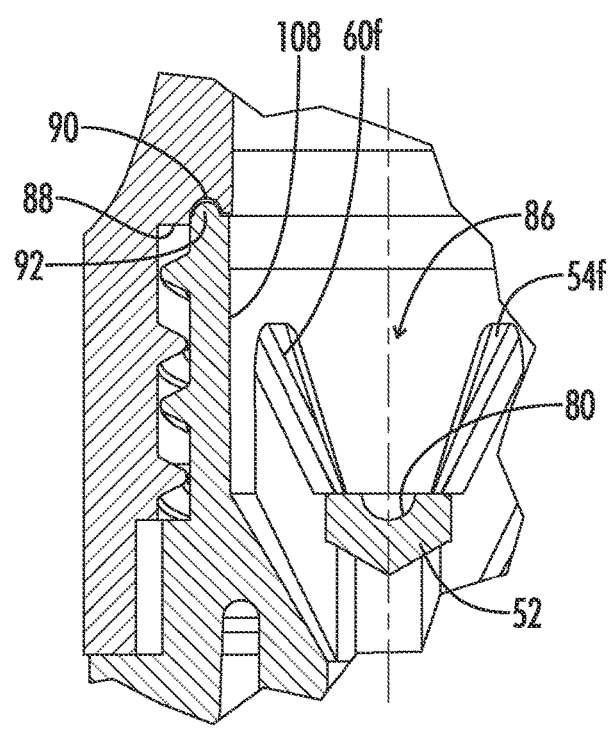
FIG. 6 is an enlarged view of the portion of the body circled in FIG. 3.

As best seen in the enlarged view of FIG. 6, the first mating structure 34 includes an inner cylindrical surface 108 extending distally from the open proximal end 46. The inner cylindrical surface 108 has a first inner diameter 110. The axial passage 50 of the male luer connection 48 has a second inner diameter 51 smaller than the first inner diameter 110. The transverse passages 62, 64, 66 and 68 are partially frusto-conical in shape tapering from the first inner diameter 110 to the second inner diameter 51.

Figure 23:
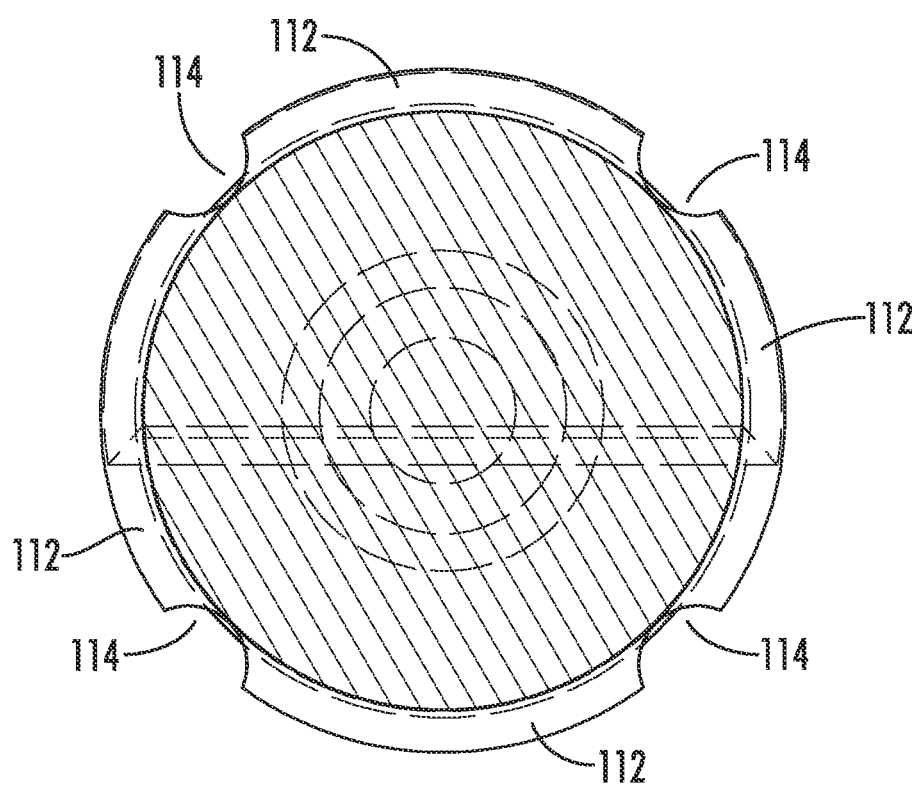
FIG. 23 is a cross-section view of the flexible valve member of FIG. 19 taken along line 23-23 of FIG. 20.

The details of the flexible valve member 76 are best seen in FIGS. 19-23. The proximal end portion 78 of flexible valve member 76 is configured to be sealingly received in the female luer connection 70 of the second mating structure 36. Below the proximal end portion 78 is a segmented stop surface 112 configured to abut lower taper 73 of the second mating structure 36 to prevent the flexible valve member 76 from being pushed out of the second mating structure 36 due to internal pressure. The segmented stop surface may include four segments as seen in FIG. 23, separated by gaps such as 114. Below segmented stop surface 112 a relatively large lateral notch 116 is formed in flexible valve member. Notch 116 is designed to cause the flexible valve member 76 to collapse in an asymmetrical manner as schematically represented in FIG. 2 when the male luer fitting 72 pushes downward on the flexible valve member 76. This causes the flexible valve member 76 to be displaced laterally relative to the longitudinal axis 38 when the flexible valve member 76 is moved from its closed position of FIG. 1 to its open position of FIG. 2. The lowermost portion of flexible valve member 76 tapers at 118 to the distal end 82 and the centering protrusion 84.

The injection port assembly 30 may be assembled from the first mating structure 34, second mating structure 36 and flexible valve member 76 substantially as follows. The flexible valve member 76 may be placed in the second mating structure 36 with the proximal end portion of the flexible valve member 76 adjacent or received in the female luer connection 70 substantially as shown in FIG. 1. Then the external threads 98 of the first mating structure 34 may be engaged with the internal threads 102 of the second mating structure 36 and the threaded connection made up until the ridge 92 sealingly engages the groove 90 and the distal end 100 of second mating structure 36 bottoms out on the proximally facing step 94 of the first mating structure 34. The ratchet lock provided by the first and second ratchet portions 98 and 104 will prevent the threads from disengaging. The first and second annular ratchet portions 98 and 104 are preferably arranged such that the second mating structure 36 bottoms out on the proximally facing step 94 of the first mating structure 34 just as the ratchet teeth have reached an engagement position as shown in FIG. 8. During the assembly of the first and second mating portions 34 and 36 the tapered guide 86 formed by the sloping faces of the ribs will guide the distal end portion 82 of the flexible valve 76 toward the base 52 so that the central protrusion 84 is received in the centering recess 82.

The use of the injection port assembly 30 is best illustrated in FIGS. 1 and 2. In FIG. 1 the injection port assembly is shown with the flexible valve member 76 in a closed position. A male luer fitting 72 is shown above the injection port assembly 30 in a position just prior to engaging the flexible valve member 76. In FIG. 2, the male ler fitting 72 has been moved downward and engaged with the upper end of the flexible valve member 76 to displace the flexible valve member 76 relative to the central body axis 38 upon entry of the male luer fitting 72 into the female luer connection 70 thereby placing the male luer fitting 72, and particularly the interior thereof, in communication with the interior 71 of the second mating structure 36.

Embodiment of FIGS. 24-38

FIGS. 24-38 illustrate a second embodiment of an injection port assembly generally designated by the numeral 130. The injection port assembly 130 differs from the injection port assembly 30 in two primary ways. First the manner in which the first and second mating structures are connected together has been changed to a welded connection. Second the design of the flexible valve member has been modified.

Figure 24:
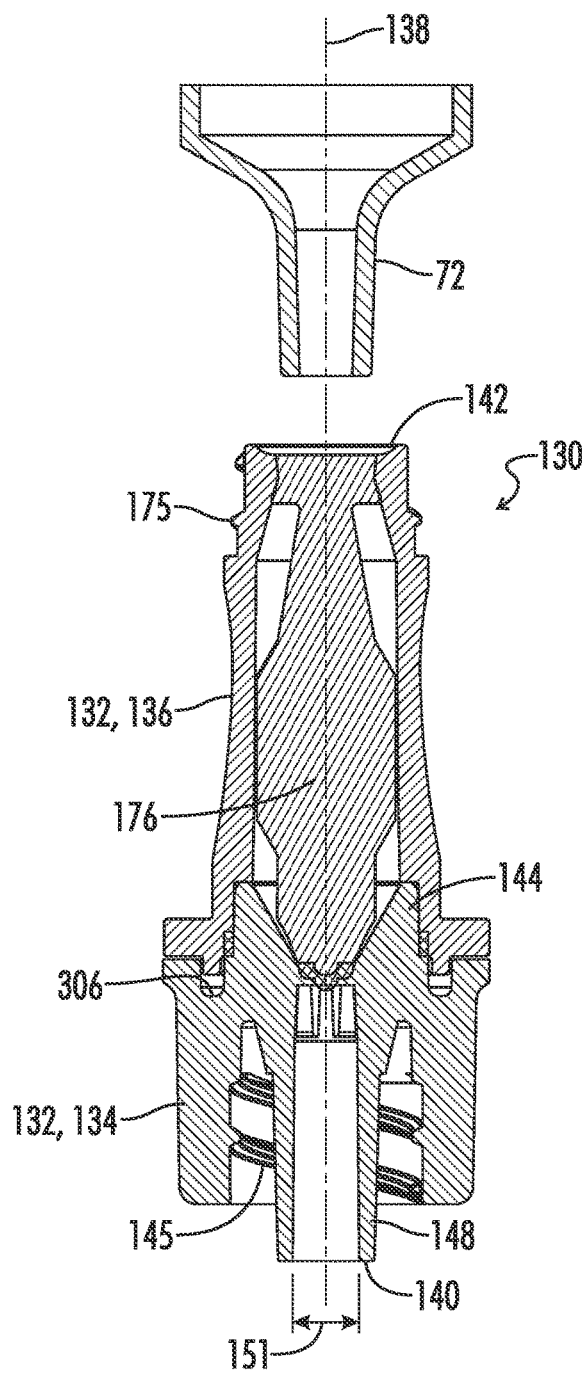
FIG. 24 is a cross-section elevation view of a second embodiment of an injection port assembly with the flexible valve member in a closed position. A male luer syringe tip is shown above the injection port assembly prior to engaging the flexible valve member.

Referring now to the drawings and particularly to FIG. 24 an injection port assembly is shown and generally designated by the number 130. The injection port assembly 130 may also be referred to as an intermittent needleless connector 130. The injection port assembly 130 includes a body 132 including a first mating structure 134 and the second mating structure 136 configured to be coupled to the first mating structure 134. Each of the first and second mating structures 134 and 136 may be a separate integrally molded plastic part.

The body 132 has a central body axis 138 extending from a distal body end 140 defined on the first mating structure 134 to a proximal body end 142 defined on the second mating structure 136.

The first mating structure 134 includes an annular wall 144 defining an open proximal end 146 of the first mating structure 134 facing toward the proximal body end 142. A male luer connection 148 includes an axial passage 150 extending from a distal end 140 of the male luer connection which is coincident with the distal end 140 of the body 132. The open proximal end 146 may also be referred to as a first mating structure proximal end 146. Annular wall 144 may also be referred to as an outer wall 144 and extends distally past a base 152 and includes an internal thread 145 concentric with the male luer connection 148.

Figure 30:
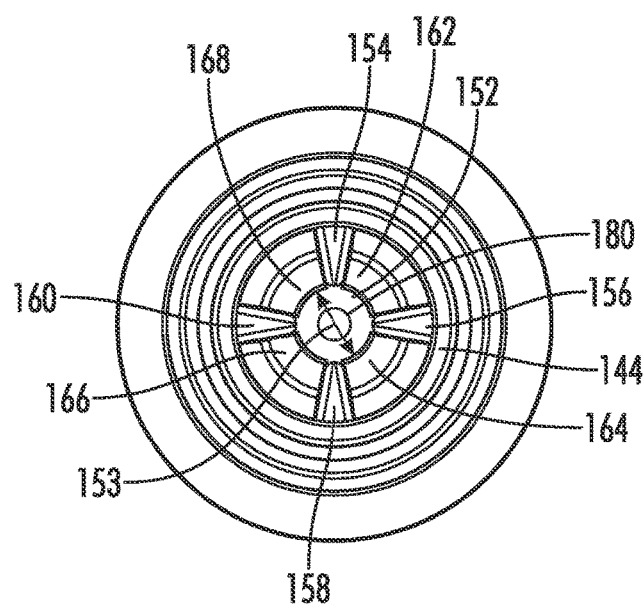
FIG. 30 is a top plan view of the first mating structure or lower body part of FIG. 28.
Figure 31:
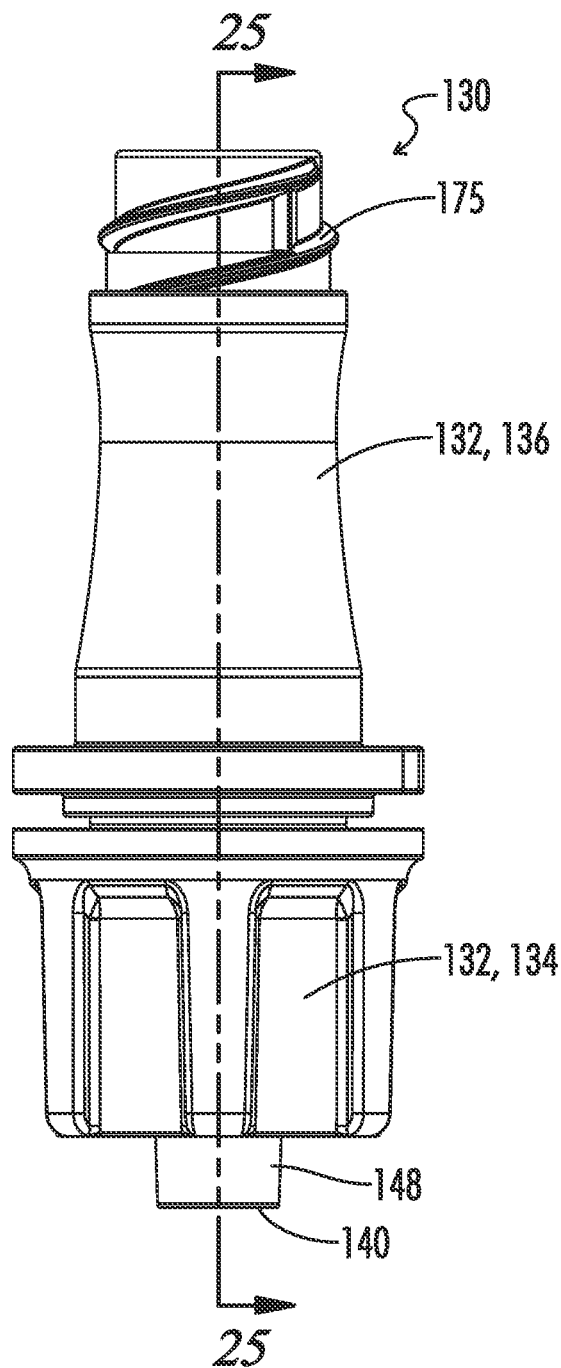
FIG. 31 is an elevation view of the injection port assembly of FIG. 24.
Figure 32:
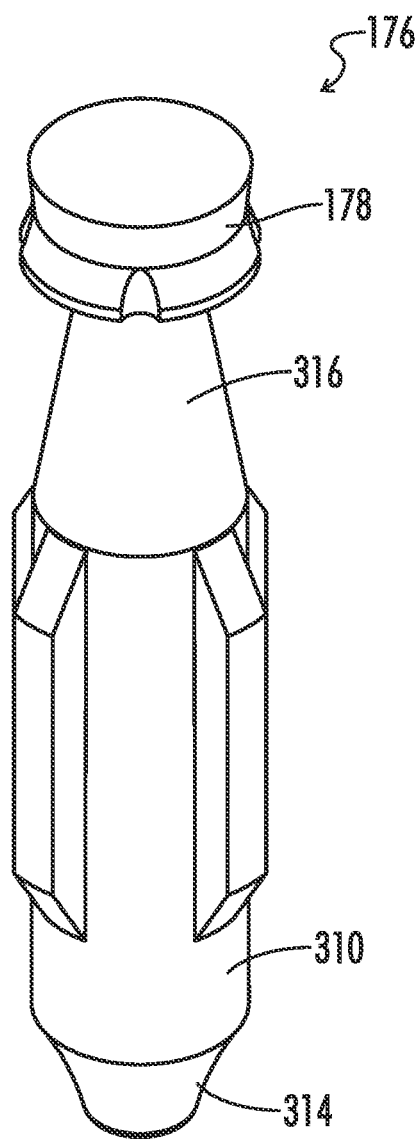
FIG. 32 is a top perspective view of the flexible valve member of the injection port assembly of FIG. 24.
Figure 33:
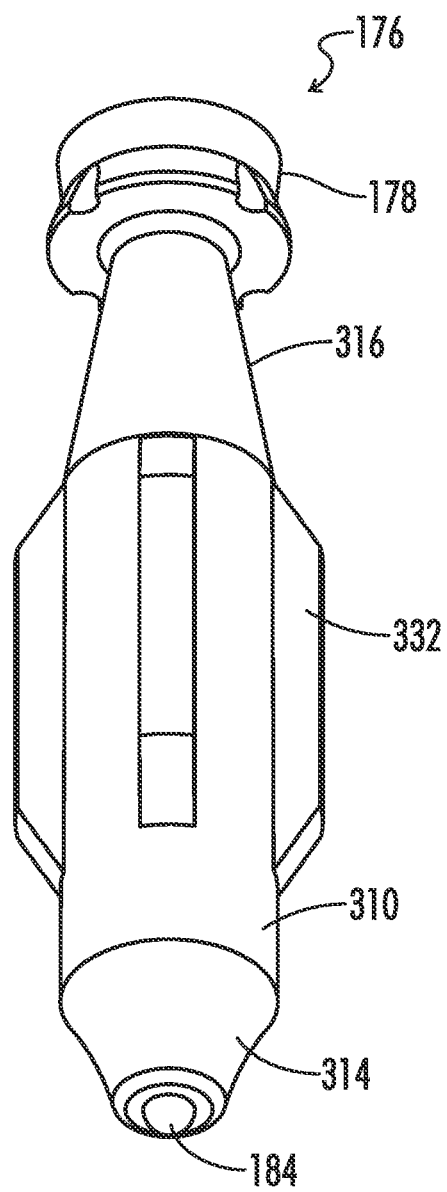
FIG. 33 is a bottom perspective view of the flexible valve member of the injection port assembly of FIG. 24.

The base 152 is centered on the body axis 138 and at least partially blocks the axial passage 150. As best seen in FIG. 30 a plurality of circumferentially spaced ribs 154, 156, 158 and 160 extend from the annular wall 144 to the base 152 and define a plurality of transverse passages 162, 164, 166 and 168 between the circumferentially spaced ribs. The transverse passages are communicated with the axial passage 150 of the male luer connection 148. The transverse passages may also be described as bypassing the base 152 to communicate an inner surface 208 of the first mating structure 134 with the axial passage 150 of the male luer connection 148. The base 152 may also be described as spanning the body axis 138 and being supported from the outer wall 144. The base 152 may also be described as being located axially between the open proximal end 146 of the first mating structure 134 and the axial passage 150 of the male luer connection 148.

The axial passage 150 has an inside diameter 151. The base 152 has a base outside diameter 153 substantially equal to the inside diameter 151 of the axial passage 150 of the male luer connection 148.

The use of the multiple transverse passages 162, 164, 166 and 168 provides a combined flow path from the open proximal end 146 to the axial passage 150 that is relatively unrestricted. The passages 162, 164, 166 and 168 have a combined cross-sectional flow area at least as great as, and preferably greater than, the cross-sectional area of the axial passage 150. Also the passages 162, 164, 166 and 168 are preferably sloped in a range of from 40 to 60 degrees relative to the longitudinal axis 138. In this manner the flow path through the passages 162, 164, 166 and 168 does not restrict the flow of fluids through the injection port assembly 130, thus providing what may be referred to as a high fluid flow injection port assembly. The flow path is non-tortuous and the passages 162, 164, 166 and 168 are free of dead ends or spaces that are difficult to flush of blood and other fluids.

Figure 25:
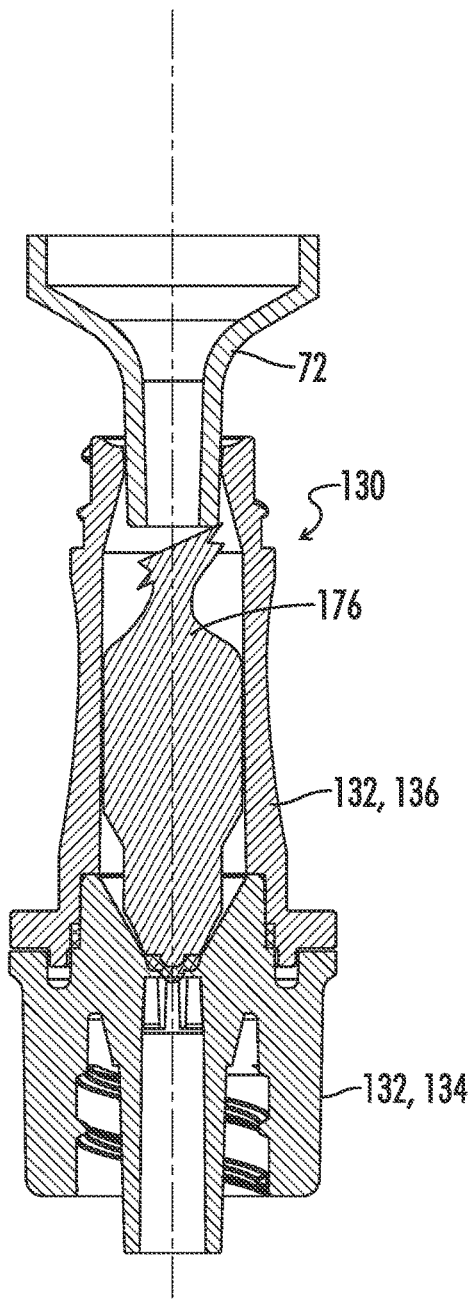
FIG. 25 is a cross-section elevation view of the injection port assembly of FIG. 24 showing the male luer syringe tip engaging the flexible valve member so that the flexible valve member is moved to an open position. The cross-section of FIG. 25 is taken along line 25-25 of FIG. 31.
Figure 27:
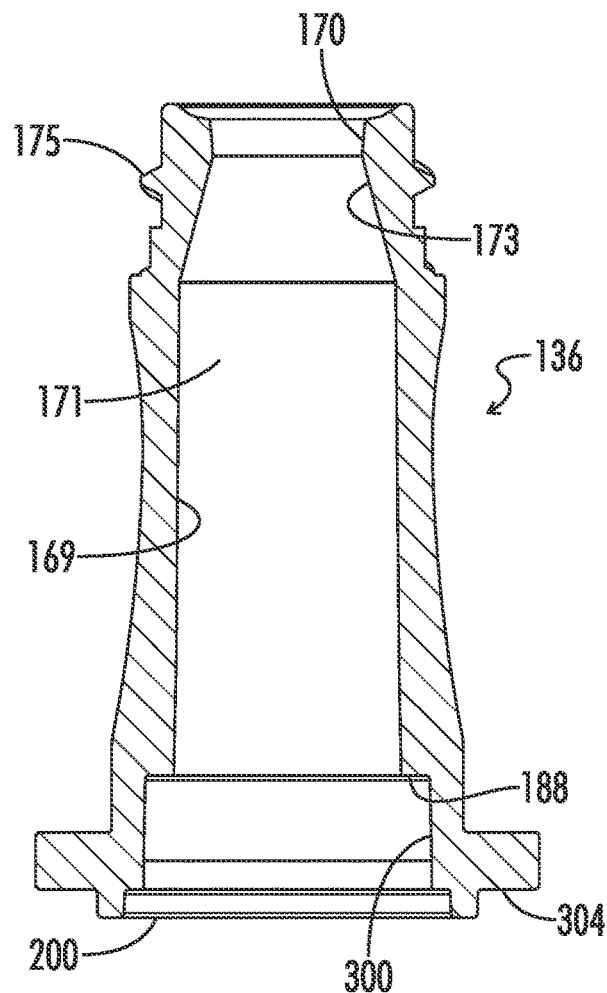
FIG. 27 is a cross-sectional elevation of the second mating structure or upper body part of the body of FIG. 26.
Figure 26:
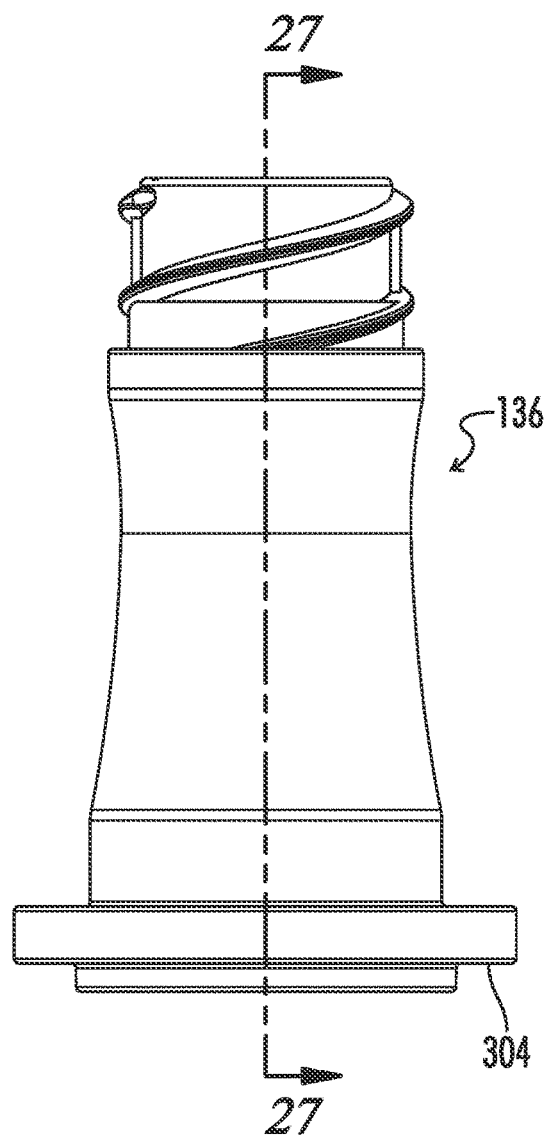
FIG. 26 is an elevation view of the second or upper mating structure of FIG. 24.

The second mating structure 136 includes a female luer connection 170 configured to receive a male luer fitting 72 (see FIGS. 24 and 25). The second mating structure 136 has an inner wall 169 defining an interior 171 communicating the female luer connection 170 with the open proximal end 146 of the first mating structure 134. The upper end of the second mating structure 136 carries an external thread 175 that can be engaged with a luer-lock connector (not shown).

A flexible valve member 176 is mounted on the base 152 of the first mating structure 134 and has a proximal valve end portion 178 configured to be sealingly received in the female luer connection 170 of the second mating structure 136 when the flexible valve member 176 is in a closed position as seen in FIG. 24. The flexible valve member 176 is configured to be displaced relative to the central body axis 138 upon entry of the male luer fitting 72 into the female luer connection 170 to thereby place the male luer fitting 72 in communication with the interior 171 of the second mating structure 136.

The first mating structure 134 includes a centering recess 180 defined in the base 152 and facing the proximal body end 142. The flexible valve member 176 includes a distal end 182 having a central protrusion 184 received in the centering recess 180.

Figure 29:
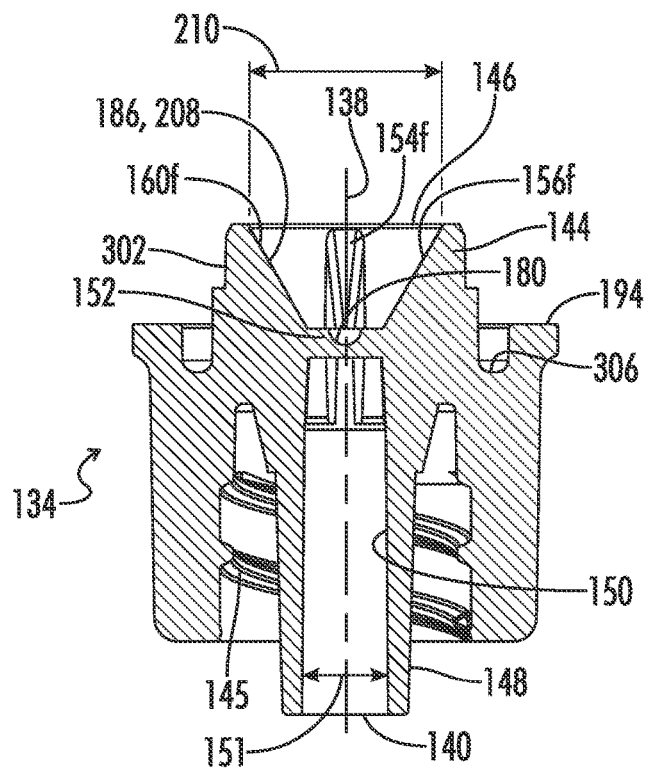
FIG. 29 is a cross-sectional elevation of the first mating structure or lower body part of the body of FIG. 28.
Figure 28:
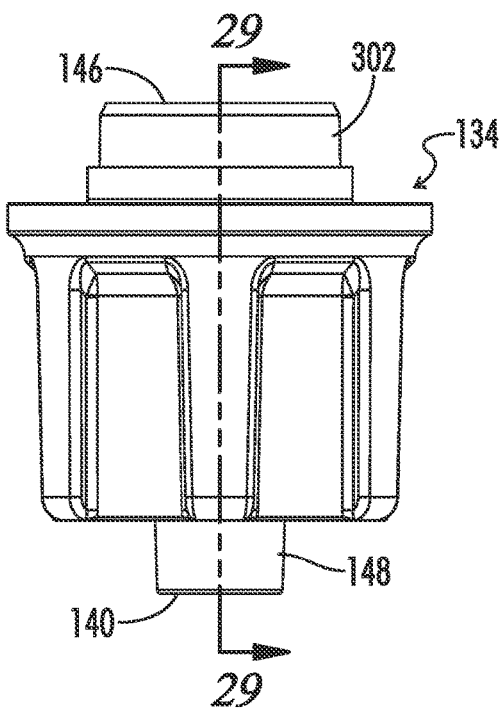
FIG. 28 is an elevation view of the first or lower mating structure of FIG. 24.

As is best seen in FIG. 29 each of the ribs 154, 156, 158 and 160 has a proximal end face such as 154f, 156f, 160f sloping distally from a radially outer end of the rib to a radially inner end of the rib attached to the base 152, so that the proximal end faces of the ribs define a tapered guide 186 for guiding the distal end 182 of the flexible valve member 176 into engagement with the base 152.

The second mating structure 136 includes an annular radially inner distally facing step 188. The open proximal end 146 of the first mating structure 134 abuts the distally facing step 188 of the second mating structure 136 when the first and second mating structures 134 and 136 are coupled together as shown for example in FIGS. 24 and 25. The second mating structure 136 may also include a cylindrical inner surface 300 located between the second mating structure distal end 200 and the radially inner distally facing step 188. The distal end 200 of the second mating structure 136 may also include a radially outwardly extending lower end face 304.

The first mating structure 134 may also include a radially outer proximally facing step 194 and a cylindrical outer wall surface 302 located between the proximal end 146 and the radially outer proximally facing step 194.

The injection port assembly 130 may be assembled from the first mating structure 134, second mating structure 136 and flexible valve member 176 substantially as follows. The flexible valve member 176 may be placed in the second mating structure 136 with the proximal end portion of the flexible valve member 176 adjacent or received in the female luer connection 170 substantially as shown in FIG. 24. Then the cylindrical outer wall surface 302 of the first mating structure 134 is closely received in the cylindrical inner surface 300 of the second mating structure 136 until the radially outwardly extending lower end face 304 of the distal end 200 of the second mating structure 136 abuts the radially outer proximally facing step 194 of the first mating structure 134. During this assembly the tapered lower end 314 of the flexible valve member 176 is guided by guide 186 into engagement with the base 152, so that center protrusion 184 is received in centering recess 180. The assembly is then placed in a sonic welding machine and sonic energy is applied to cause the first and second mating structures 134 and 136 to be sonically welded together along the interface between surfaces 300 and 302 and along the engagement of the radially outwardly extending lower end face 304 of the distal end 200 of the second mating structure 136 with the radially outer proximally facing step 194 of the first mating structure 134. Any weld slag or other debris generated during the sonic welding operation may be received in an annular groove 306 which is formed in the radially outer proximally facing step 194 of the first mating structure 134.

As best seen in FIG. 29, the first mating structure 134 includes an inner surface 208 extending distally from the open proximal end 46. The inner surface 208 has a first inner diameter 210 at its upper end. The axial passage 150 of the male luer connection 148 has a second inner diameter 151 smaller than the first inner diameter 210. The transverse passages 162, 164, 166 and 168 are partially frusto-conical in shape tapering from the first inner diameter 210 to the second inner diameter 151.

Figure 38:
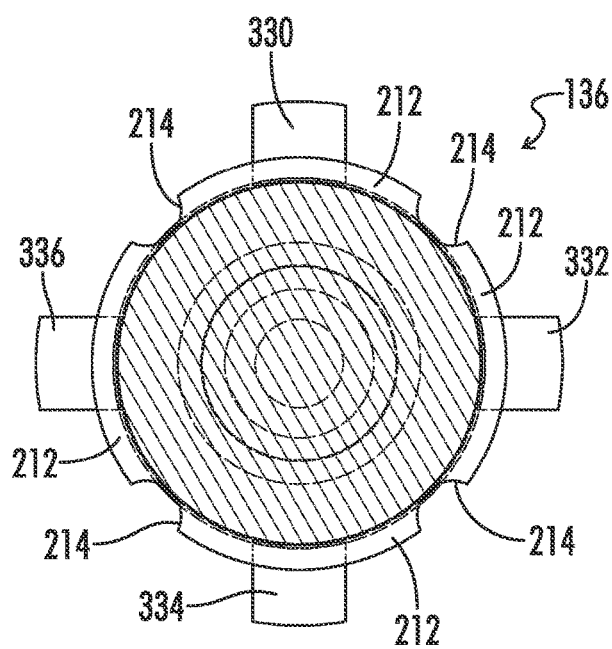
FIG. 38 is a plan section view of the flexible valve member of FIG. 34, taken along line 38-38 of FIG. 34.

The details of the flexible valve member 176 are best seen in FIGS. 32-38. The proximal end portion 178 of flexible valve member 176 is configured to be sealingly received in the female luer connection 170 of the second mating structure 136. Below the proximal end portion 178 is a segmented stop surface 212 configured to abut lower taper 173 of the second mating structure 136 to prevent the flexible valve member 176 from being pushed out of the second mating structure 136 due to internal pressure. The segmented stop surface may include four segments as seen in FIG. 38, separated by gaps such as 214.

The flexible valve member 176 includes an axially extending main body portion 310 which is preferably cylindrical in shape having a main body portion diameter 312. A tapered distal end portion 314 extends distally from the main body portion 310 and includes the distal end 182 and the protrusion 184. A tapered proximal portion 316 extends proximally from the main body portion 310 and joins the proximal end portion 178.

The flexible valve member 176 has an axial length 318. Proximal end portion 178 has an axial length 320. Tapered proximal portion 316 has an axial length 322. Main body portion 310 has an axial length or main body portion length 324. Tapered distal end portion 314 has an axial length 326.

The main body portion length 324 may be at least one-half the axial length 318 of the flexible valve member 176.

The axial length 322 of the tapered proximal portion 316 may be greater than the main body portion diameter 312, and preferably may be greater than 125% of the main body portion diameter 312. The tapered proximal portion 316 may taper from the main body portion diameter 312 at its junction with main body portion 310 to a minimum outside diameter 328 less than 60% of the main body portion diameter 312.

Figure 34:
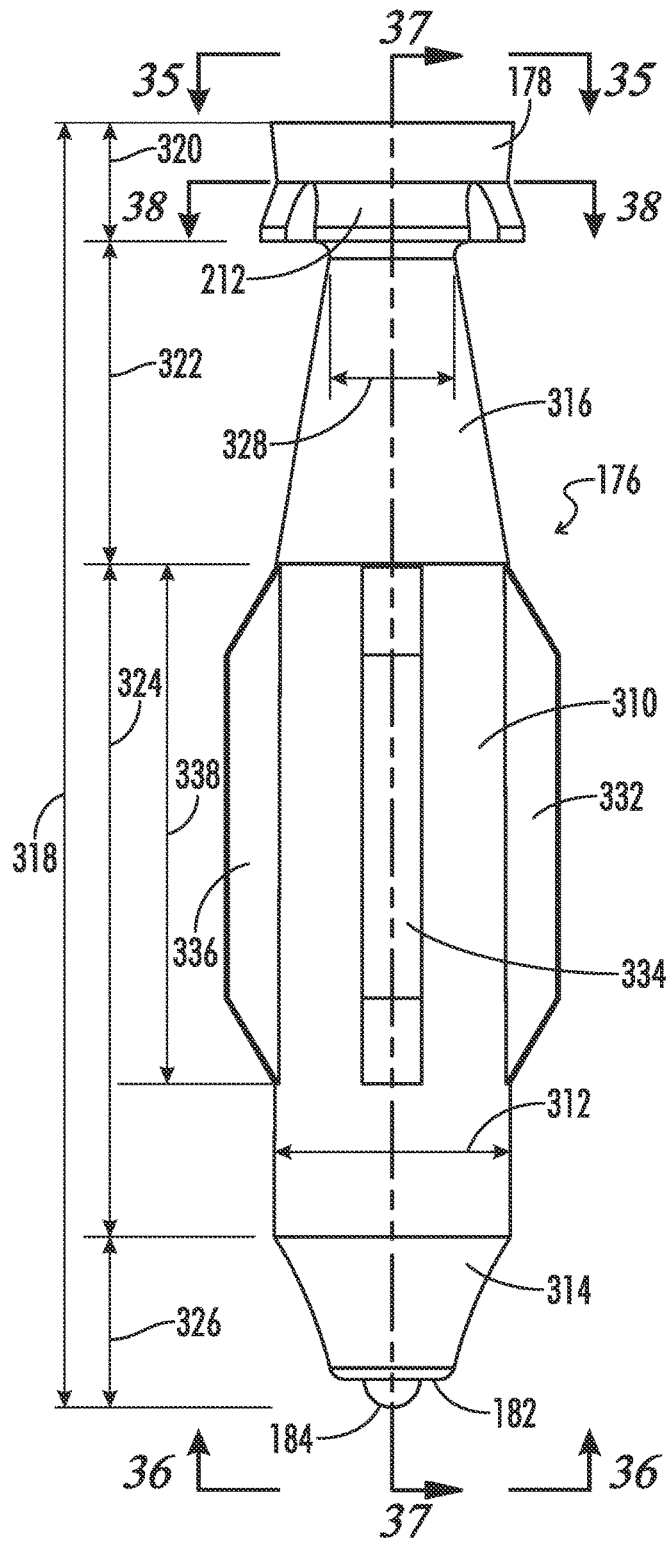
FIG. 34 is a side elevation view of the flexible valve member of the injection port assembly of FIG. 24.
Figure 35:
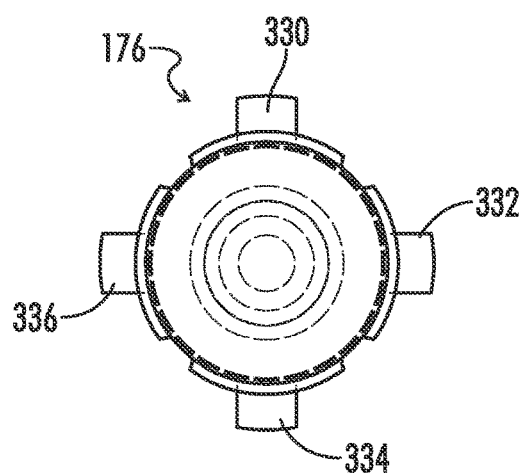
FIG. 35 is a top plan view of the flexible valve member of FIG. 34, taken along line 35-35 of FIG. 34.
Figure 36:
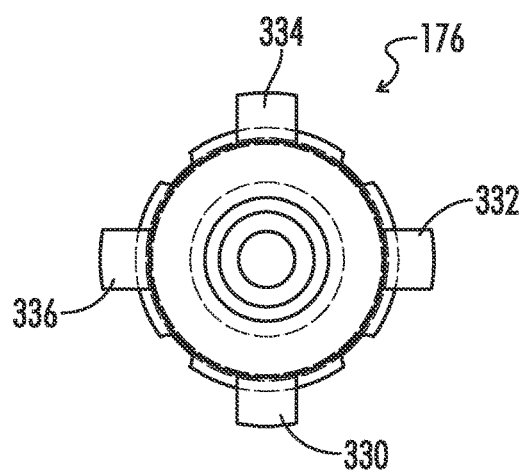
FIG. 36 is a bottom view of the flexible valve member of FIG. 34, taken along line 36-36 of FIG. 34.
Figure 37:
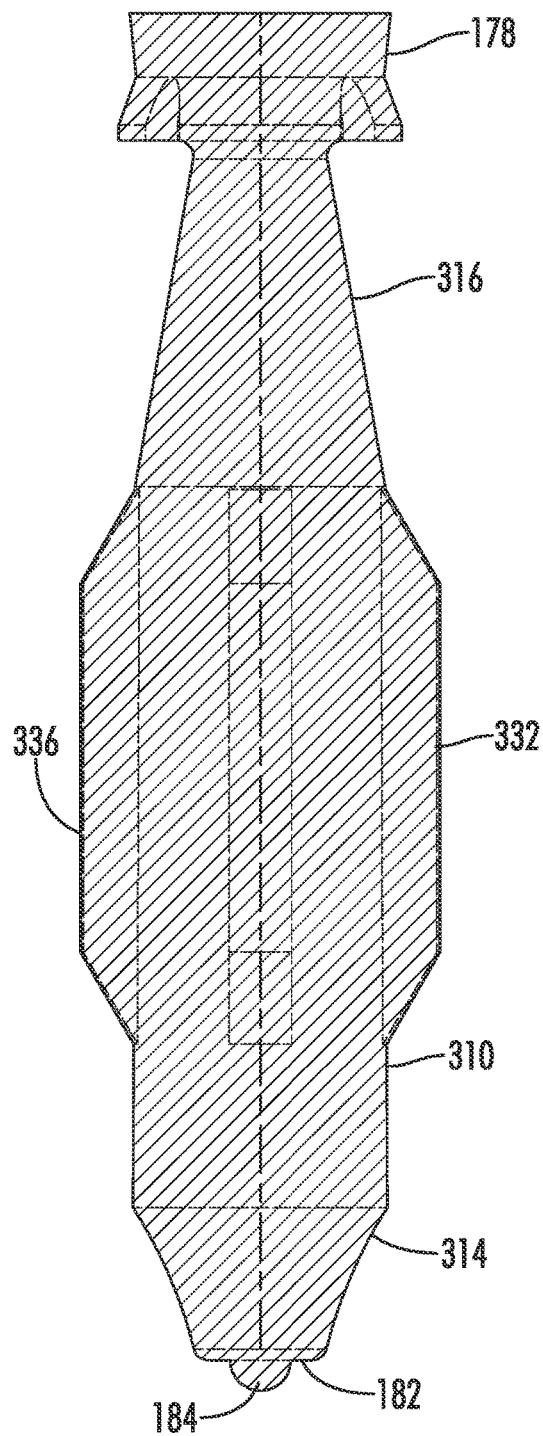
FIG. 37 is an elevation section view of the flexible valve member of FIG. 34, taken along line 37-37 of FIG. 34.

The flexible valve member 176 includes a plurality of stabilizing fins 330, 332, 334 and 336 extending laterally, and preferably radially, outward from the main body portion 310 toward the interior wall 169 of the second mating structure 136. As best seen in FIG. 34 the fins may extend along a fin length 338 which is less than the axial length 324 of the main body portion 310.

The flexible valve member 176 is constructed from a resilient elastomeric material such that the flexible valve member 176 can deflect as shown in FIG. 25 when engaged by the male luer fitting 72, and can rebound back to its original shape to reseal against the female luer connection 170 when the male luer fitting 72 is withdrawn.

The use of the injection port assembly 130 is best illustrated in FIGS. 24 and 25. In FIG. 24 the injection port assembly is shown with the flexible valve member 176 in a closed position. A male luer fitting 72 is shown above the injection port assembly 130 in a position just prior to engaging the flexible valve member 176. In FIG. 25, the male luer fitting 72 has been moved downward and engaged with the upper end of the flexible valve member 176 to displace the flexible valve member 176 relative to the central body axis 138 upon entry of the male luer fitting 72 into the female luer connection 170 thereby placing the male luer fitting 72, and particularly the interior thereof, in communication with the interior 171 of the second mating structure 136.

The function of the flexible valve member 176 when engaged by the male luer fitting 72 to move the flexible valve member 176 from the closed position of FIG. 24 to the open position of FIG. 25 is generally as follows. The stabilizing fins 330-336 keep the main body portion 310 centered in the body 132 even as the flexible valve member 176 begins to axially compress as the male luer fitting 72 begins to push downwardly on the proximal valve end portion 178. Because the tapered proximal portion 316 has the smallest cross-section and is relatively long, the tapered proximal portion 316 will ultimately buckle and be displaced laterally relative to the center axis 138 as is schematically represented in FIG. 25. When the tapered proximal portion 316 buckles the male luer fitting 72 will be in fluid communication with the interior 171 of the second mating structure 136 and can then introduce fluid into or withdraw fluid from the interior 171.

Thus it is seen that the apparatus and methods of the present invention readily achieve the ends and advantages mentioned as well as those inherent therein. While certain preferred embodiments of the invention have been illustrated and described for purposes of the present disclosure, numerous changes in the arrangement and construction of parts and steps may be made by those skilled in the art, which changes are encompassed within the scope and spirit of the present invention as defined by the appended claims.

What is claimed is:

1. An injection port assembly, comprising:
a body including a first mating structure and a second mating structure configured to be coupled to the first mating structure, the body having a central body axis extending from a distal body end defined on the first mating structure to a proximal body end defined on the second mating structure;
the first mating structure including:
an annular wall defining an open proximal end of the first mating structure facing toward the proximal body end;
a male luer connection including an axial passage extending from a distal end of the male luer connection toward the proximal body end; and
an internal passage communicating the open proximal end of the first mating structure with the axial passage of the male luer connection;
the second mating structure including a female luer connection configured to receive a male luer fitting, the second mating structure having an interior wall defining an interior communicating the female luer connection with the open proximal end of the first mating structure; and
a flexible valve member including:
a proximal valve end portion configured to be sealingly received in the female luer connection of the second mating structure when the flexible valve member is in a closed position;
an axially extending main body portion;
a tapered distal end portion extending distally from the main body portion and configured to engage the first mating structure;
a tapered proximal portion extending proximally from the main body portion to the proximal valve end portion, the tapered proximal portion being axially longer than the tapered distal end portion;
a plurality of stabilizing fins extending laterally outward from the main body portion toward the interior wall of the second mating structure; and
wherein the tapered proximal portion is configured to buckle asymmetrically relative to the central body axis upon entry of the male luer fitting into the female luer connection to thereby place the male luer fitting in communication with the interior of the second mating structure.

2. The injection port assembly of claim 1, wherein:
the main body portion of the flexible valve member is cylindrical in shape having a main body portion diameter.

3. The injection port assembly of claim 2, wherein:
the main body portion of the flexible valve member has a main body portion length at least one-half an axial length of the flexible valve member.

4. The injection port assembly of claim 3, wherein:
the tapered proximal portion of the flexible valve member tapers from the main body portion diameter to a minimum outside diameter less than 60% of the main body portion diameter.

5. The injection port assembly of claim 4, wherein:
the tapered proximal portion of the flexible valve has an axial length greater than the main body portion diameter.

6. The injection port assembly of claim 4, wherein:
the tapered proximal portion of the flexible valve has an axial length greater than 125% of the main body portion diameter.

7. The injection port assembly of claim 2, wherein:
the tapered proximal portion of the flexible valve member tapers from the main body portion diameter to a minimum outside diameter less than 60% of the main body portion diameter.

8. The injection port assembly of claim 7, wherein:
the tapered proximal portion of the flexible valve has an axial length greater than the main body portion diameter.

9. The injection port assembly of claim 7, wherein:
the tapered proximal portion of the flexible valve has an axial length greater than 125% of the main body portion diameter.

10. The injection port assembly of claim 1, wherein:
the main body portion of the flexible valve member has a main body portion length at least one-half an axial length of the flexible valve member.

* * * * *